(12) United States Patent
Liu et al.

(10) Patent No.: US 11,959,054 B2
(45) Date of Patent: Apr. 16, 2024

(54) SUBSTRATE APPARATUS WITH MULTI-LAYER SUBSTRATE FOR CELL-BASED MEAT CULTIVATORS

(71) Applicant: Upside Foods, Inc., Berkeley, CA (US)

(72) Inventors: Ryan Jiajong Liu, Berkeley, CA (US); Jaewon Samuel Kang, Oakland, CA (US)

(73) Assignee: Upside Foods, Inc., Berkeley, CA (US)

( * ) Notice: Subject to any disclaimer, the term of this patent is extended or adjusted under 35 U.S.C. 154(b) by 4 days.

(21) Appl. No.: 17/755,761

(22) PCT Filed: Nov. 4, 2021

(86) PCT No.: PCT/US2021/058126
§ 371 (c)(1),
(2) Date: May 6, 2022

(87) PCT Pub. No.: WO2023/080894
PCT Pub. Date: May 11, 2023

(65) Prior Publication Data
US 2023/0272318 A1    Aug. 31, 2023

(51) Int. Cl.
*C12M 3/00*    (2006.01)
*C12M 1/00*    (2006.01)
*C08J 5/18*    (2006.01)

(52) U.S. Cl.
CPC ............ *C12M 21/08* (2013.01); *C12M 23/34* (2013.01); *C08J 5/18* (2013.01)

(58) Field of Classification Search
CPC ................................ B29C 53/36; C12M 23/34
See application file for complete search history.

(56) References Cited

U.S. PATENT DOCUMENTS 9,534,206 B2    1/2017 Davis et al.
9,969,966 B2    5/2018 Asgari
(Continued)

FOREIGN PATENT DOCUMENTS

TW    92112990       5/1992
WO    WO 2010/032260 A1    3/2010
(Continued)

OTHER PUBLICATIONS

International Search Report & Written Opinion as received in PCT/US2021/058126 dated Jul. 26, 2022.

*Primary Examiner* — Andrew D Graham
(74) *Attorney, Agent, or Firm* — Keller Preece PLLC

(57) ABSTRACT

The present disclosure relates to a substrate apparatus (and methods of manufacturing the same) with one or more substrates having a substrate spacing for growing a cell mass. In particular embodiments, the disclosed substrate apparatus includes a substrate wound into a coiled configuration with an intra-coil spacing between coil layers. To provide the intra-coil spacing, certain implementations use a separator. For example, a separator is applied to a substrate surface, and the separator-substrate combination is wound together (e.g., around a spool). In turn, a locking element is attached to the substrate to maintain the coiled configuration. The separator is then removed via heat treatment, chemical treatment, or physical displacement—thereby leaving the intra-coil spacing between the coil layers. Alternatively, no separator is used to provide a substrate spacing. For example, in lieu of a separator, the locking element is actively applied to the substrate during the winding process.

10 Claims, 22 Drawing Sheets

(56) References Cited

U.S. PATENT DOCUMENTS

| | | |
|---|---|---|
| 11,147,300 B2 | 10/2021 | Leung et al. |
| 2002/0182241 A1* | 12/2002 | Borenstein ............. C12M 21/08 |
| | | 428/188 |
| 2008/0127477 A1* | 6/2008 | Chen ....................... B29C 53/42 |
| | | 29/428 |
| 2009/0136717 A1* | 5/2009 | Kihara ................ B29C 66/1282 |
| | | 428/189 |
| 2010/0094404 A1* | 4/2010 | Greenhalgh .............. A61F 2/82 |
| | | 623/23.72 |
| 2011/0111484 A1* | 5/2011 | Muller-Feuga ........ C12M 21/02 |
| | | 156/213 |
| 2011/0197555 A1* | 8/2011 | Schildermans ..... F01N 13/0097 |
| | | 55/482 |
| 2012/0115179 A1* | 5/2012 | Hauden ................ G01N 1/2813 |
| | | 435/283.1 |
| 2014/0093618 A1 | 4/2014 | Forgacs et al. |
| 2015/0064779 A1* | 3/2015 | Schultz .................. G01B 11/08 |
| | | 264/40.1 |
| 2015/0360450 A1* | 12/2015 | Barbaroux ............. C12M 23/28 |
| | | 428/518 |
| 2019/0336649 A1* | 11/2019 | Béduer ................. C12M 23/34 |
| 2020/0039111 A1* | 2/2020 | Tsumura ................. B29B 11/16 |
| 2021/0024868 A1 | 1/2021 | Ferrie et al. |
| 2021/0047599 A1* | 2/2021 | Castillo .................. C12M 23/22 |
| 2022/0105510 A1* | 4/2022 | O'Boyle ............ F16K 99/0059 |

FOREIGN PATENT DOCUMENTS

| | | | |
|---|---|---|---|
| WO | WO 2019/175442 A1 | 9/2019 | |
| WO | WO 2020/061387 A1 | 3/2020 | |
| WO | WO-2020061387 A1 * | 3/2020 | ............ C12M 23/06 |
| WO | WO 2021/108093 A1 | 6/2021 | |
| WO | WO 2021/108094 A1 | 6/2021 | |

* cited by examiner

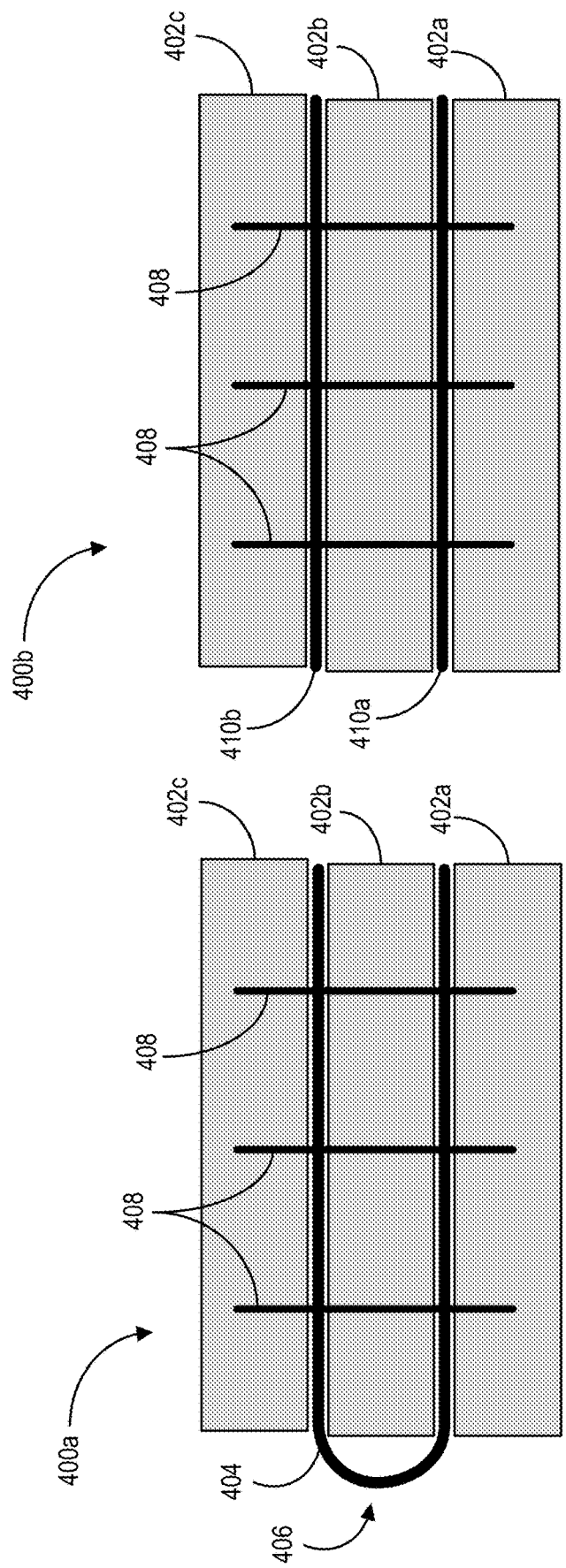

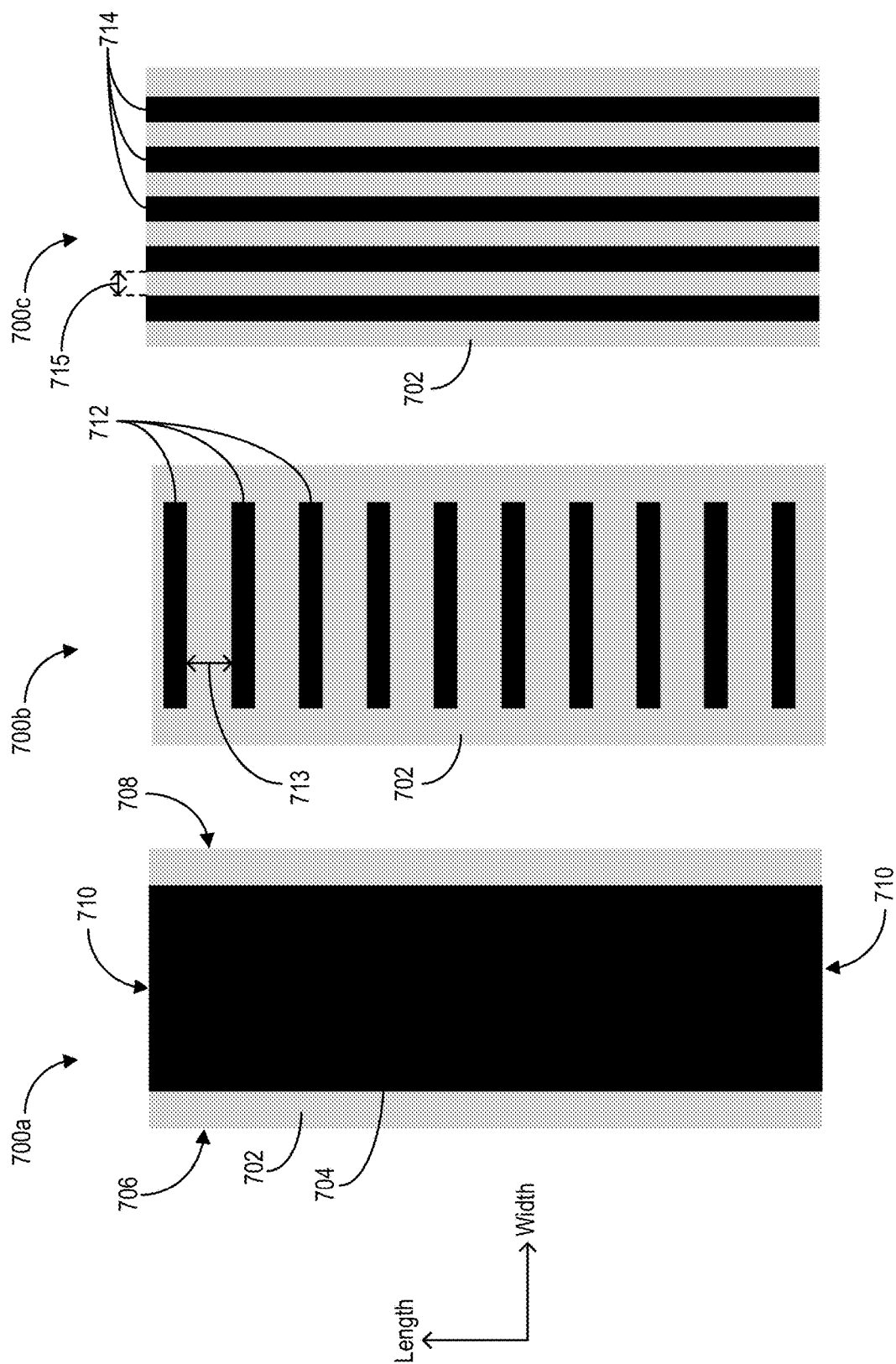

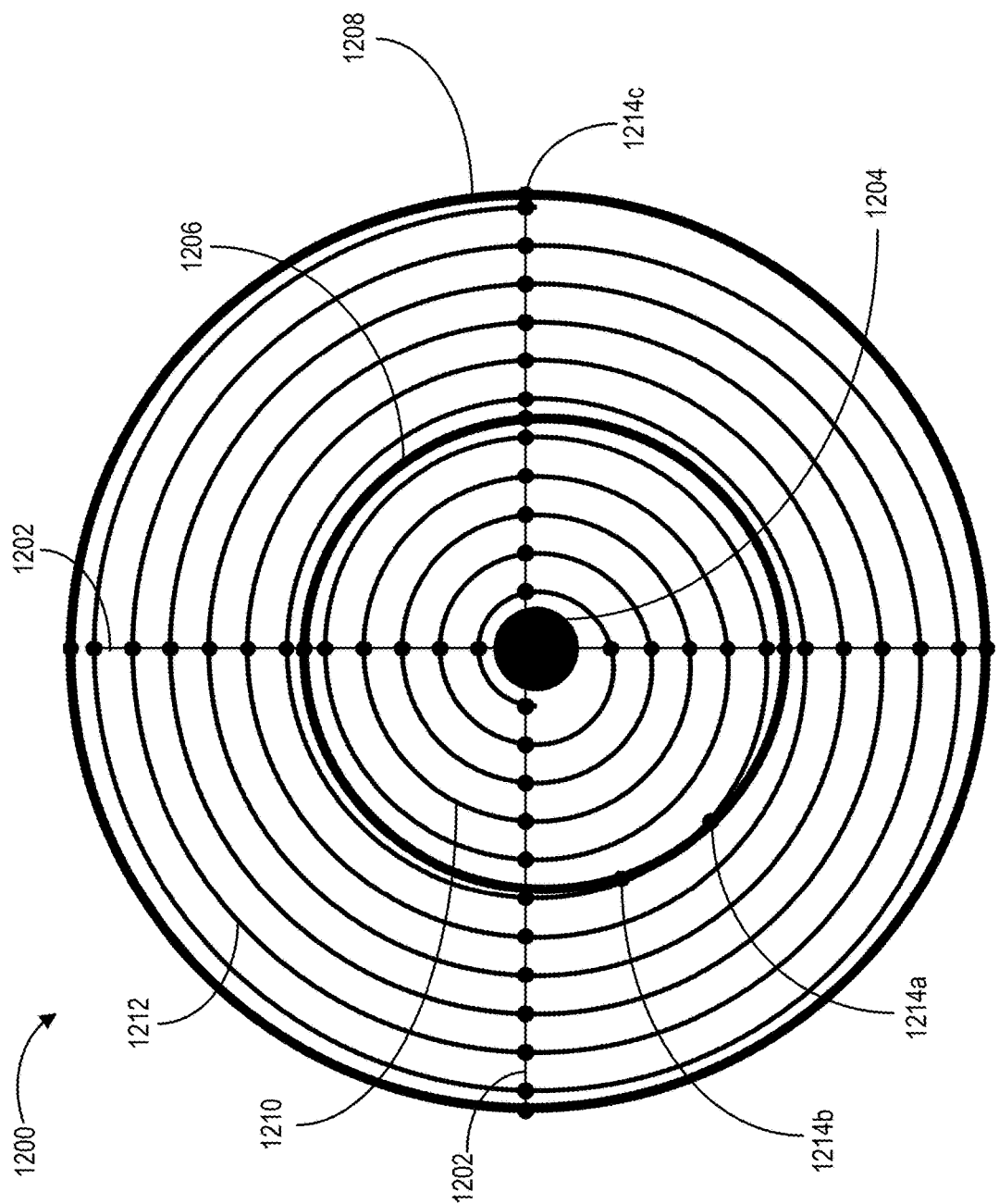

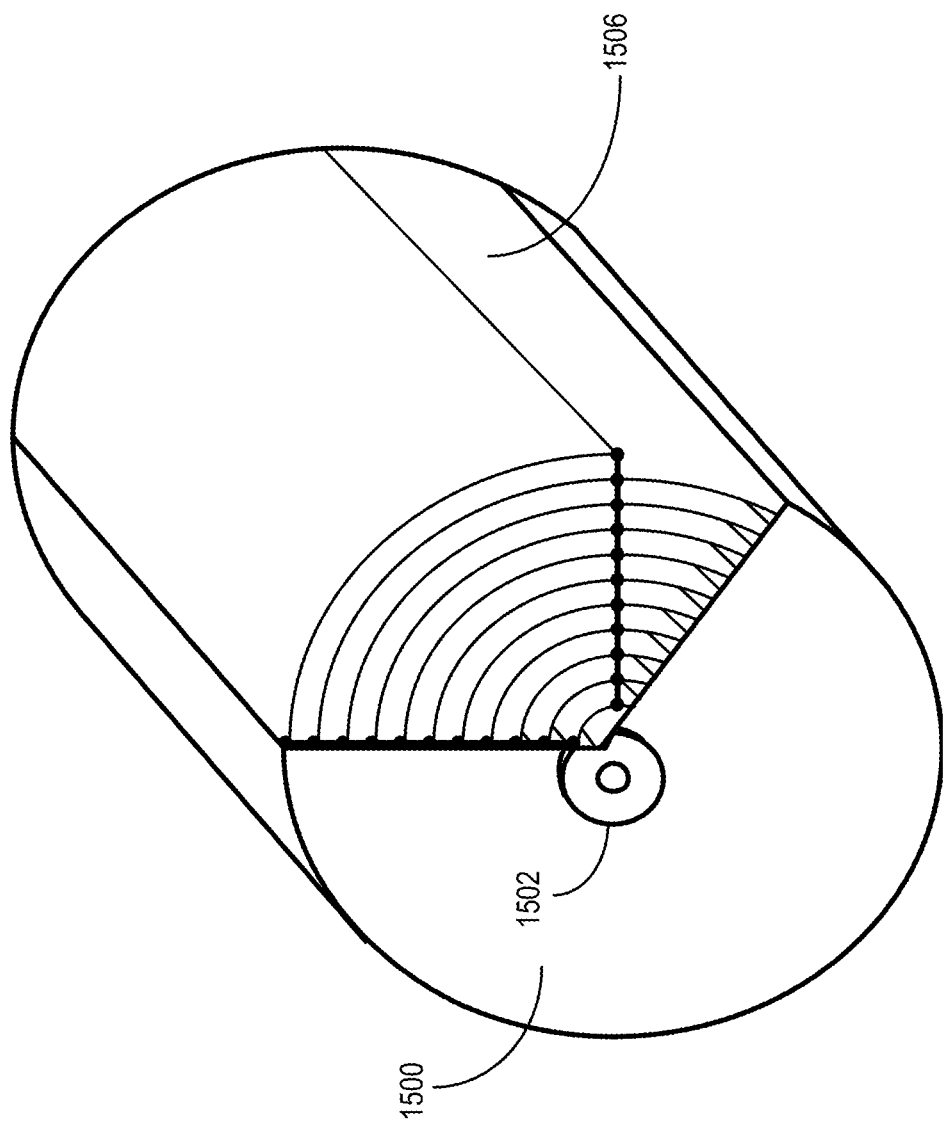

SUBSTRATE APPARATUS WITH MULTI-LAYER SUBSTRATE FOR CELL-BASED MEAT CULTIVATORS

BACKGROUND

The present disclosure relates to multi-layered substrates, and more particularly, to an apparatus comprising multi-layered substrates for growing cultured meat and a method of manufacturing the same.

Lab-grown or cultured meat belongs to the emerging field of cellular agriculture and represents a promising technology for delivering products that have so far been produced through livestock. This technological innovation aims to offer a possibility of reducing the negative effects of conventional meat production techniques on humans, livestock, and the environment. As part of these advancements, cell culture substrates have been utilized to support attachment, proliferation, and differentiation of cells. In some tissue engineering applications, cell culture substrates include various types and designs, such as three-dimensional substrates (e.g., scaffolds) or two-dimensional substrates (e.g., petri dish) configured to support the formation of single and multilayered cellular sheets. However, there remains a need for substrates and corresponding methods of manufacturing that can improve manufacturability, promote various processes from seeding to harvesting of cell masses, and decrease risk of contamination.

The subject matter claimed herein is not limited to embodiments that solve any disadvantages or that operate only in environments such as those described above. Rather, this background is only provided to illustrate one example technology area where some embodiments described herein may be practiced.

BRIEF SUMMARY

Embodiments of the present disclosure include apparatuses and methods of manufacturing that relate to one or more elongated substrates having a substrate spacing for growing a cell mass. In particular embodiments, the disclosed apparatuses include an elongated substrate wound into a coiled configuration with an intra-coil spacing between coil layers. To provide consistent and uniform intra-coil spacing, in certain implementations a removable separator is used. For example, a removable separator is applied to a surface of the elongated substrate, and the separator-substrate combination is wound together (e.g., around a spool). The removable separator spaces each coil layer apart according to a thickness of the removable separator. In turn, a locking element is attached to the elongated substrate to maintain the coiled configuration. The removable separator is then removed via heat treatment, chemical treatment, or physical displacement—thereby leaving the intra-coil spacing between the coil layers.

Alternatively, in other implementations, no separator is used to provide a substrate spacing. For example, in lieu of a removable separator, the locking element is actively applied to the elongated substrate during the winding process. To illustrate, a locking element can be attached to a first coil layer during a first winding revolution. Subsequently, the locking element can be attached to each newly formed coil layer during subsequent winding revolutions.

Additional or alternative embodiments are also herein contemplated. Indeed, various features and advantages of one or more embodiments of the present disclosure are outlined in the following description.

BRIEF DESCRIPTION OF THE DRAWINGS

The detailed description provides one or more embodiments with additional specificity and detail through the use of the accompanying drawings, as briefly described below.

FIGS. 4A-4B illustrate schematic side views of substrate apparatuses that include stacked planar substrate layers in accordance with one or more embodiments.

FIGS. 7A-7E illustrate plan views of substrate-separator configurations for winding or stacking in accordance with one or more embodiments.

FIG. 12 illustrates a side view of a substrate apparatus with inner, intermediate, and outer support structures in accordance with one or more embodiments.

FIGS. 15A-15C illustrate a bioreactor for implementing with a substrate apparatus in accordance with one or more embodiments.

DETAILED DESCRIPTION

Figure 1:
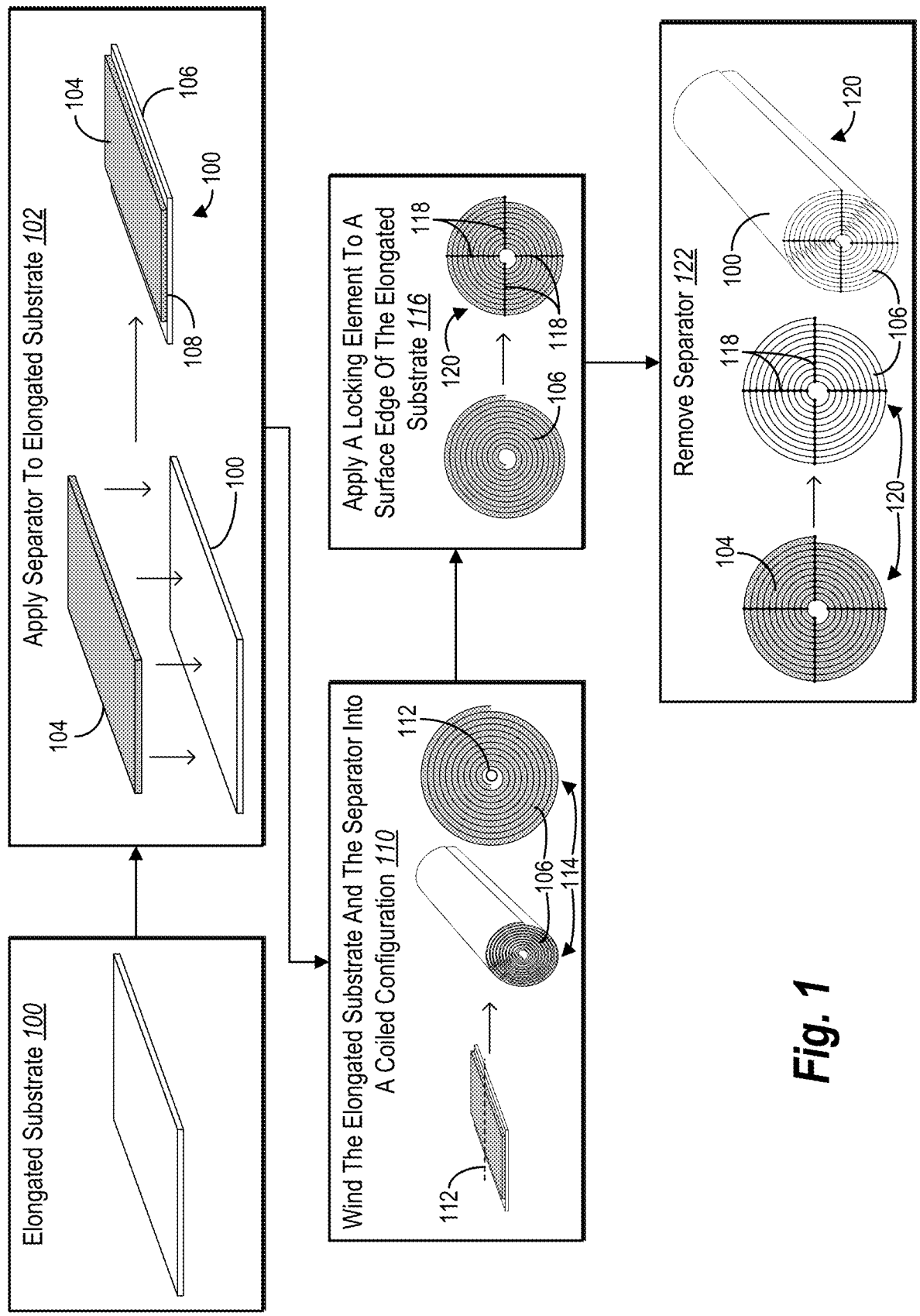
FIG. 1 illustrates a process flow for manufacturing a substrate apparatus in accordance with one or more embodiments.

This disclosure describes one or more embodiments of a substrate apparatus to insert into a bioreactor to grow a cell mass. In some embodiments, the substrate apparatus includes (i) a substrate formed into layers, (ii) a removable separator for maintaining spacing between the layers, and/or (iii) a locking element to fix the edges of the formed substrate layers in place. The removable separator may be placed on a surface of a substrate (e.g., a sheet of stainless steel). As the separator-substrate combination is wound together (e.g., around a spool), the thickness of the removable separator controls the gap between coil layers of the substrate. During or after winding, a locking element is affixed to the substrate for holding in place a shape and spacing of the substrate in the wound (coiled) configuration. For example, the locking element connects to a surface edge of the substrate via one or more of spot welds or brazing. If present, the removable separator is subsequently removed from between the substrate coil layers (e.g., via thermal, chemical, electrical, or physical means). The substrate, however, remains locked in the coiled configuration with the desired intra-coil spacing to grow a cell mass on the substrate surface inside a bioreactor cavity.

As just mentioned, in some embodiments, the substrate apparatus includes a substrate, removable separator, and a locking element. The following provides a brief overview of these and other elements of the substrate apparatus—including some example embodiments. Elements of the substrate apparatus are discussed in turn, beginning with the substrate (also referred to as an "elongated substrate"). In one or more embodiments, the substrate supports or promotes the adhesion, differentiation, and/or growth of cells to form a cell mass—namely, a comestible meat product. For example, the substrate is configured to receive cultured cell media as part of a seeding process inside a bioreactor. Once the cell mass grows to a predetermined size or for a predetermined duration, the cell mass is harvested from the substrate (e.g., via a high-velocity fluid flow, biophysical methods).

In addition, the substrate can include a variety of different materials and features. To illustrate, in one or more embodiments, the substrate includes a patterned texture (e.g., as described in U.S. Patent Pub. No. 2021/0106032 A1, entitled APPARATUSES AND METHODS FOR PREPARING A COMESTIBLE MEAT PRODUCT, filed on Dec. 22, 2020, the contents of which are expressly incorporated herein by reference). Further, the substrate comprises one or more bio-compatible materials, such as a metal material or polymer material. For example, in some embodiments, the substrate comprises one or more of polylactic acid, starch derived materials, waxes (e.g., paraffin, beeswax), oils (e.g., food derived substance like coconut oil), polychlorotrifluoroethylene, polyetherimide, polysulfone, polystyrene, polycarbonate, polypropylene, silicone, polyetheretherketone, polymethylmethacrylate, nylon, acrylic, polyvinylchloride, vinyl, phenolic resin, petroleum-derived polymers, glass, polyethylene, terephthalate, titanium, aluminum, cobalt-chromium, chrome, silicates, glass, alloys, ceramics, carbohydrate polymer, mineraloid matter, and combinations or composites thereof. In general, materials with relatively low melting points, such as waxes, that are solid at room temperature but melt at slightly higher temperatures are preferable. Ideally, the substrate is solid during storage without temperature control and requires little energy input to liquify—thereby resulting in a more economic and environmentally friendly process.

In particular embodiments, the substrate includes stainless steel (e.g., an austenitic stainless steel, a ferritic stainless steel, a duplex stainless steel, a martensitic and precipitation hardening stainless steel, a passivated stainless steel). For example, the substrate includes food grade stainless steel, such as grade 316 stainless steel, or grade 430 stainless steel (e.g., for enhanced corrosion resistance). Alternatively, the substrate includes a shape-memory material (e.g., a nickel titanium alloy, Nitinol) that retains or can revert back to a predetermined shape. In certain implementations, metal materials can provide increased cleanability and/or sterilization. In contrast, polymer materials can provide increased cell adhesion properties and facilitate additional manufacturing methods (e.g., injection molding or extrusion) not available to certain metals.

As indicated above, the substrate can also include substrate layers. Accordingly, the substrate apparatus of the present disclosure may include one or more of a variety of different substrate layer configurations. For example, in some embodiments, the substrate includes a single substrate wound around itself in a continuous fashion forming coil layers in a coiled configuration. In particular embodiments, the substrate winds around a spool (e.g., a shaped spool, as discussed below) that corresponds to a rotational axis for the substrate apparatus. In certain implementations, the coiled configuration includes a cylindrical form factor (e.g., a circular cross-section of coil layers). In other embodiments, the coil configuration includes different form factors. For example, the coil configuration can include an ovular form factor (e.g., an oval-shaped cross-section of coil layers), a conical form factor (e.g., a cone-shaped cross-section of coil layers), or other polygonal form factor.

In other embodiments, the substrate includes multiple substrate layers in non-coiled configurations. For example, in particular embodiments, the substrate comprises multiple stacked substrates (e.g., a first substrate stacked over or under a second substrate). To illustrate, stacked substrates can include stacked planar (plate-like) substrates, stacked lampshade (conical-shaped) substrates, or other shaped substrates stacked on top of each other.

In addition to the substrate, one or more embodiments of the substrate apparatus also include a separator (also referred to as a "removable separator"). In particular embodiments, the separator includes a spacer or spacer material configured for application to a surface of a substrate. For example, the separator includes a spacer of a certain height (i.e., thickness) that, when applied to a substrate surface, controls the spacing between subsequently formed layers of the substrate apparatus. That is, the separator can reduce or prevent touch points between substrate layers in their various configurations (e.g., coiled configurations, stacked configurations, etc.). Accordingly, the separator can be wound with the substrate or otherwise inserted in between substrate layers via one or more application processes.

Like the substrate, the separator can also include myriad different configurations. For example, in some embodiments, the separator includes a continuous spacer sheet that substantially covers a surface of a substrate. For instance, the separator can be sized and shaped to include a length dimension and a width dimension similar to the substrate (where the length dimension is perpendicular to the rotational axis of the substrate, and the width dimension is parallel to the rotational axis). In certain instances, the separator includes a smaller width than the substrate (e.g., an offset of about two inches, about six inches, or about ten inches from the surface edge of the substrate) to avoid interference with attaching a locking element to the substrate.

In other embodiments, the separator is not continuous. For example, the separator includes a plurality of strips. The plurality of strips may be positioned along a length or a width of the substrate. Additionally, the plurality of strips can include a predetermined or customizable spacing interval between strips and/or relative to other components of the substrate apparatus, such as a locking element or surface edge of the substrate. In one or more embodiments, the plurality of strips includes a predetermined or customizable height (e.g., thickness) that can depend on the spacing intervals between strips. For instance, increased thickness of the plurality of strips may be advantageous with larger spacing intervals, and decreased thickness of the plurality of strips may be advantageous with smaller spacing intervals (e.g., to help prevent substrate touch points). A noncontinuous separator also advantageously requires less spacer material. In addition, a noncontinuous separator may be faster to dissolve because there is less material to dissolve. Further, a noncontinuous separator can include an increased amount of surface area—thereby accommodating increased exposure to dissolving fluids (whether gas or liquid) across top and side surfaces of the noncontinuous separator.

Additionally or alternatively, the separator is positioned on or attached to the substrate in a particular way that facilitates subsequent removal of the separator. For example, in some embodiments, the separator overhangs a surface edge of the substrate (e.g., such that the separator can be pulled out via the overhanging portion). As another example, the separator includes a perforated edge such that the separator can easily shear away from the substrate during removal.

As just alluded to, the separator can be removed in a variety of different ways. Indeed, in some embodiments, the separator can be pulled, pushed, scraped, media blasted, fluid (e.g., gas or liquid) blasted, or otherwise physically displaced from between substrate layers. In other embodiments, the separator is removed via chemical means. For example, the separator can be dissolved utilizing one or more solvents, acids, or enzymes. To illustrate, in certain implementations, the separator is removed via water or alcohol (e.g., at elevated temperatures). In some embodiments, the substrate is entirely or substantially removed.

In at least some embodiments, dissolving (or partially dissolving) the separator leaves a coating (e.g., a peptide layer, a sticky veneer, etc.) on the substrate surface that promotes cell adhesion or growth and/or enhances cleanability of the substrate. Alternatively, partially dissolving the separator leaves a porous material, such as a metallic foam inside of which cells can enter and grow. In other embodiments, dissolving (or otherwise removing the separator) can leave etchings or patterned textures in the substrate to provide enhanced cell adhesion properties to the substrate.

In certain embodiments, the separator is removed via exposure to elevated fluid temperature, elevated pressure environments, lowered pressure environments, and/or other biological instigators. For instance, the separator may melt or fall out from between substrate layers when exposed to a hot gas or liquid, electricity or high voltage, conductive heating, gas pressurization, ultraviolet lighting, ultrasonic vibrations (e.g., from an ultrasonic bath), or some combination thereof either simultaneously or sequentially.

It will be appreciated that the separator can include a number of different materials. In one or more embodiments, the separator includes a bio-compatible, non-toxic material for interfacing with a substrate surface. For example, the separator can be compatible with cell adhesion or cell growth on a substrate surface. Additionally, for example, the separator does not render the substrate unsafe for growing a comestible food product. For instance, the separator includes one or more plant-based materials (e.g., starch or sucrose-derived materials). Alternatively, the separator includes a suitable artificial material, such as polystyrene.

In particular embodiments, the separator includes an incompressible or substantially incompressible material (e.g., a material with one or more properties modeled according to an isotropic elastic material, a neo-Hookean material, a Mooney-Rivlin material, or a Holmes-Mow material). To illustrate, in certain embodiments, the separator includes a wax material, polymethyl methacrylate, polystyrene, polycarbonate, styrene-butadiene rubber, polyvinyl acetate, vulcanized natural rubber, nitrile-butadiene rubber, aromatic polyimide, polyurethane, etc.

Additionally or alternatively, the separator comprises other materials and/or material properties. For example, the separator includes a dissolvable material. In another example, the separator includes a material with a lower melting point than a substrate melting point. In yet another example, the separator comprises a material that is environmentally friendly or treatable to become environmentally friendly. For instance, once removed, the separator can be post-processed (e.g., re-casted, re-molded, re-shaped, cleaned, etc.) for re-use as a separator for an additional substrate apparatus. Alternatively, a removed separator may be used for other secondary applications (e.g., cell attachment facilitator) and is preferably easily decomposable and otherwise environmentally friendly.

In one or more embodiments, the substrate apparatus includes a locking element. In particular embodiments, the locking element comprises one or more stabilizing or securing structures that maintain a position of substrate layers. For example, the locking element includes a securing structure that attaches to a surface edge of a substrate (e.g., at each layer of the substrate) to maintain a spacing between substrate layers and a shaped configuration of the substrate. To illustrate, the locking element can include one or more spokes, struts, filaments, screens, grates, plates, etc. in a variety of configurations connected to the surface edge of the substrate (e.g., via one or more of spot welds or brazing).

The locking element can also include various different materials. For example, the locking element comprises a biocompatible material and/or a corrosion resistant material. In some embodiments, the locking element comprises a same material as the substrate. For instance, the locking element comprises a stainless steel (e.g., for welding to the substrate). In other instances, the locking element comprises a metal material with a lower melting point than the substrate (e.g., for brazing to the substrate). In additional or alternative embodiments, the locking element comprises one or more of polyolefins (e.g., polyethylene and polypropylene), polyvinyl chlorides, or fluoropolymers (e.g., polyvinylfluoride, polyvinylidene fluoride, polytetrafluoroethylene, polychlorotrifluoroethylene, perfluoroalkoxy polymer, fluorinated ethylene-propylene, polyethylenetetrafluoroethylene, polyethylenechlorotrifluoroethylene, perfluorinated elastomer, vinylidene-fluoride-based copolymers, tetrafluoroethylene-propylene, perfluoropolyether). In one or more embodiments, the locking element comprises silicone. In other embodiments, the locking element comprises material for a carbon-fiber component, a three-dimensional printed component, and/or an injection-molded component.

In one or more embodiments, the locking element is applied post-winding or post-stacking of substrate layers. Indeed, in certain embodiments implementing a separator, the locking element maintains a substrate positioning and layer spacing after removal of the separator. Alternatively, in one or more embodiments without a separator, the locking element can be actively applied to the substrate (e.g., during the winding process or stacking process). For example, as the substrate is wound into a coiled configuration, the locking element can actively attach to the surface edge of the substrate at predetermined turn progressions or revolution intervals. To illustrate, a robot, automated system, or technician can spot weld, braze, solder, or otherwise attach the locking element to the surface edge of a current substrate layer as infeed elements (e.g., dynamic rollers) position the current substrate layer for a precise spacing relative to an adjacent substrate layer.

In one or more embodiments, the substrate apparatus further includes a spool. The spool includes a core or central support structure for winding the substrate into a coiled configuration. Accordingly, in certain embodiments, the spool comprises a shaped spool to achieve certain form factors of the substrate in the coiled configuration. For example, the spool includes a cylindrical spool, an ovular (oval-shaped) spool, a triangle-shaped spool, a rectangular-prism-shaped spool, a conical-shaped spool, or other polygonal-shaped spool (e.g., square, pentagon, etc.).

It will be appreciated that myriad other embodiments of the substrate apparatus are contemplated within this disclosure. For example, in certain embodiments, the substrate apparatus includes a pre-shaped substrate. To illustrate, prior to winding or during winding, the substrate may be plastically deformed to generate a certain substrate shape, generate an initial set of coil layers with a preliminary intra-coil spacing, or provide additional rigidity to the substrate. In a similar fashion, the substrate can be plastically deformed by being overwound and subsequently released to a deformed resting coil. Alternatively, the substrate may include a shape memory material that, when treated or shaped, retains (or reverts back) to a predetermined shape as may be desired.

As another example, inner, intermediate, and/or outer support structures may be added to the substrate apparatus to provide increased rigidity to the substrate in the coiled configuration (particularly at outer coil layers where the substrate may be prone to buckling on itself). For instance, an inner set of coil layers may be disposed between an inner support structure and an intermediate support structure. Likewise, an outer set of coil layers may be disposed between the intermediate support structure and an outer support structure. In turn, the locking element can connect each of the coil layers and the support structures to distribute the substrate load across the support structures, increase substrate rigidity, and help prevent buckling.

In another alternative embodiment, the substrate apparatus can include multiple substrate layers that are wound together. For example, rather than winding a single substrate into multiple coil layers, the substrate apparatus can include parallel substrates stacked on top of each other and wound around a rotational axis (and/or spool) to form parallel spirals. Advantageously, parallel spirals can improve flow control by facilitating multi-directional flow via the dual fluid channels.

In yet another alternative embodiment, the substrate apparatus can include a ring of individual nubs (e.g., permanent separators) positioned along a surface of the substrate near the surface edge. Then, upon winding the substrate, a subsequent coil layer abutting the permanent separator can be welded (or otherwise fixed) to the permanent separator. Additional rings of permanent separators can be added along the substrate surface near the opposing surface edge and/or along a center portion of the substrate surface as needed for maintaining a consistent intra-coil spacing between coil layers. This embodiment avoids application of a removable separator between coil layers and a locking element that spans across multiple coil layers at the surface edge of the substrate.

Still, in other embodiments, the substrate apparatus includes concentric substrate rings (as opposed to winding a continuous substrate). The concentric substrate rings may be manipulated to include a substrate spacing. Thereafter, a locking element can be applied to maintain the substrate spacing between substrate rings.

The substrate apparatus as disclosed herein can provide various advantages over prior substrates and bioreactor systems. In particular, a manufacturability of the substrate apparatus can be significantly improved relative to a manufacturability of prior substrates and bioreactor systems. For example, the substrate apparatus can decrease manufacturing costs by avoiding costly machining processes and hard tooling for certain permanent spacing elements (e.g., embossings) of prior substrates and bioreactor systems. Additionally, for example, the substrate apparatus can improve manufacturing flexibility. Indeed, some prior substrates and bioreactor systems require minimum substrate thicknesses so that there is sufficient substrate material on which to perform various substrate machining processes. The substrate apparatus as disclosed herein is not limited in these ways and therefore improves manufacturing processes and enables a thinner substrate, which advantageously can decrease cost and increase surface area within a bioreactor.

In addition to improved manufacturability, the substrate apparatus can reduce contamination risk prevalent in some prior substrates and bioreactor systems. For example, certain prior substrates and bioreactor systems implement permanent spacing elements that create hundreds (if not thousands) of different surface touchpoints prohibiting proper cleaning of a substrate. For instance, these touchpoints prevent baths, fluid blasting, and other cleaning methods from fully removing grown cell tissues—leading to an enhanced risk of contamination upon re-use of the substrate. These touchpoints also potentially lead to corrosion sites, which can exacerbate contamination risks and render the substrate unusable. The spacing elements of prior designs use continuous embosses as permanent spacers, rather than the temporary, removable separator of the present disclosure. In addition, the continuous embosses of prior designs had the ability to overlap and nest together, creating areas with decreased surface area and increased contact area between adjacent substrate layers. This also potentially led to variable substrate layer spacing. Preventing these issues required time- and labor-intensive separation of substrate layers to minimize contact areas. In contrast, the substrate apparatus as disclosed herein reduces or eliminates touchpoints between substrate layers compared to prior substrates and bioreactor systems (e.g., by utilizing a locking element at the surface edge of a substrate to space apart substrate layers).

Still further, the substrate apparatus can improve surface area utilization and bioreactor efficiency compared to prior substrates and bioreactor systems. As just mentioned, some prior substrates and bioreactor systems implement permanent spacing elements and/or require a minimum gauge substrate. Permanent spacing elements on the substrate surface directly reduce an available surface area for growing cell tissue. In addition, thicker substrates can lead to reduced bioreactor efficiency as there is less substrate surface that will fit inside a fixed volume bioreactor cavity. By contrast, the substrate apparatus as disclosed herein uses a locking element to maintain a desired substrate spacing between substrate layers—without limitation of substrate gauge requirements and without permanent spacers taking up substrate surface area. Accordingly, the substrate apparatus can increase an amount of available surface area for growing a cell mass compared to prior substrates and bioreactor systems (e.g., by utilizing tight substrate winds consistently spaced with small gaps). In turn, with increased available surface area, the substrate apparatus more efficiently utilizes the available volume inside a bioreactor cavity.

Turning to the figures, FIG. 1 illustrates a process flow for manufacturing a substrate apparatus 120 in accordance with one or more embodiments. As shown in FIG. 1, the process flow begins with an elongated substrate 100. In one or more embodiments, the elongated substrate 100 comprises a section of bio-compatible material for growing a cell mass inside a bioreactor. In certain embodiments, the elongated substrate 100 comprises a sheet (or roll) of stainless steel. For example, the elongated substrate 100 may include stainless steel with a gauge or thickness of about 1 millimeter, about 2.5 millimeters, about 10 millimeters, about 50 millimeters, about 1 centimeter, about 3 centimeters, or about 5 centimeters, etc. In other embodiments, the elongated substrate 100 comprises a different material and/or a different layout other than a sheet layout. Indeed, the elongated substrate 100 can include a shaped substrate (e.g., a conical-shaped substrate). Similarly, in other embodiments, the elongated substrate 100 includes a plastically deformed substrate (e.g., via pre-shaping rollers or overwinding).

At a step 102, a separator 104 may be applied to the elongated substrate 100. In one or more embodiments, the separator 104 comprises a removable, biocompatible spacer element in sheet, strip, or other layout configured to space apart coil layers of the elongated substrate 100. Specifically, a height (or thickness) of the separator 104 controls a substrate spacing between substrate layers as will be described below. Additionally, the separator 104 includes certain dimensions other than a controlling height or thickness. For example, in some embodiments, the separator 104 includes a length that is similar to (or the same as) a length of the elongated substrate 100 (e.g., such that the separator 104 is flush with or proximate to a substrate end 108). Additionally, for example, the separator 104 includes a width that is less than a width of the elongated substrate 100 (e.g., such that the separator 104 is neither flush with nor proximate to a surface edge 106). By maintaining a distance between the separator 104 and the surface edge 106, the separator 104 avoids interference with application of a locking element as will be described below.

To apply the separator 104, a number of different applicator implementations can be utilized. For example, in some embodiments, the separator 104 is adhered to the elongated substrate 100 via one or more adhesives. To illustrate, a roll or sheet of the separator 104 with adhesive may be placed on top of the elongated substrate 100. Additionally, in some cases, the separator 104 may be pressed against or rolled onto the elongated substrate 100 for smoothing and/or consistent application.

In other embodiments, the separator 104 is applied in alternative ways (depending on the type of separator). For instance, the separator 104 may be applied to the elongated substrate 100 via a spray-on application, an injection application, a molten pour-on application, a brush application, a dipping or emersion process, etc. In additional or alternative embodiments, the separator includes one or more orientations, configurations, and/or applied layouts (e.g., for certain folds, die cuts, weavings, form factors, interval spacing, directional spacing, etc.) as described further below in relation to FIGS. 4A-7E.

At a step 110, the elongated substrate 100 and the separator 104 may be wound into a coiled configuration 114. For example, as shown in FIG. 1, the elongated substrate 100 and the separator 104 are wound around a rotational axis 112 to form coil layers. Additionally, albeit not shown in FIG. 1, the elongated substrate 100 and the separator 104 can be wound around a spool (e.g., a shaped spool). In an alternative embodiment, attachment of the separator 104 to the elongated substrate 100 at the step 102 may be performed simultaneously to (e.g., during) the step 110 of winding together the separator 104 and the elongated substrate 100.

To perform the winding, an automated winding system may autonomously turn the elongated substrate 100 and the separator 104. For example, the automated winding system may clamp onto or otherwise clasp end portions of the elongated substrate 100 and the separator 104 near the substrate end 108. The automated winding system may then rotate at the rotational axis 112 such that the elongated substrate 100 and the separator 104 form coil layers. Alternatively, the automated winding system may rotatably engage a spool that is removably affixed to end portions of the elongated substrate 100 and the separator 104 near the substrate end 108. Still, in other embodiments, the elongated substrate 100 and the separator 104 are wound around the rotational axis 112 using one or more manual methods (e.g., hand rolling).

In one or more embodiments, the step 110 includes actively utilizing a tensioner or other mechanism to manage a winding tension of the elongated substrate 100 and the separator 104. For example, in some embodiments, infeed elements (e.g., tensioner rollers) progressively raise or lower to correspondingly adjust a winding tension of the elongated substrate 100 and the separator 104 being wound together. In particular embodiments, the tensioner or other mechanism maintains a constant (or near constant) tension for winding the elongated substrate 100 and the separator 104.

In the coiled configuration 114, the elongated substrate 100 and the separator 104 are tightly wrapped together. Indeed, as shown in FIG. 1, each turn or layer of the elongated substrate 100 exposed at the surface edge 106 is spaced apart according to the thickness of the separator 104. Moreover, in the coiled configuration 114, the spacing between coil layers of the elongated substrate 100 corresponds to a desired spacing for seeding a cell culture, flowing cell culture media across the cells, and growing the cells on the surface of elongated substrate 100.

At a step 116, a locking element 118 may be applied to the surface edge 106 of the elongated substrate 100 in the coiled configuration 114—thereby forming the substrate apparatus 120. In one or more embodiments, the locking element 118 locks into place a positioning of each coil layer of the elongated substrate 100 in the coiled configuration 114. In so doing, the locking element 118 holds or maintains an intra-coil spacing between coil layers—without reducing a surface area of the elongated substrate 100 and without introducing intra-coil touchpoints, as may be the case with permanent, surface spacing structures (e.g. embosses).

To apply the locking element to the elongated substrate 100, a variety of different attachment mechanisms may be implemented. In some embodiments, the locking element 118 is welded, brazed, or soldered to the elongated substrate 100 (e.g., via automated or manual processes). For example, the locking element 118 may be spot welded to each coil layer of the elongated substrate 100. As another example, the locking element 118 may be brazed to the elongated substrate 100 via emersion into a molten bath (e.g., a molten nickel bath). In other embodiments, the locking element 118 is attached to the elongated substrate 100 via one or more of adhesives, bonds, ties, fasteners (e.g., nuts, bolts, screws, compression clamps, etc.), magnets, interlocking joints (e.g., tongue-and-groove, dovetail, etc.), mating joints, and the like.

Moreover, it will be appreciated that the locking element 118 can include myriad different configurations. For example, in some embodiments, the locking element 118 comprises one or more spokes, struts, filaments, screens, grates, plates, etc. To illustrate, in certain implementations, the locking element 118 includes a set of rigid or flexible (wire-like) metal filaments that traverse across the coil layers in a perpendicular manner relative to the surface edge 106. Some example locking element configurations are further described below in relation to FIGS. 9-11.

At a step 122, the separator 104 may be removed from the substrate apparatus 120. In some embodiments, removing the separator 104 comprises physically displacing the separator 104. For example, the separator 104 may be pulled out (e.g., via an overhanging portion or a tearable portion from a perforated edge as described below in relation to FIGS. 7D-7E). Alternatively, the separator 104 may be physically displaced via pressurized fluid blasting, ultrasonic bathing, etc.

In certain embodiments, removing the separator 104 comprises using an acid, solvent, or enzyme to dissolve the separator 104. Similarly, removing the separator 104 can include melting the separator 104 (e.g., via conductive heating, convection heating, or electric-based heating of the elongated substrate 100).

In these or other embodiments, it will be appreciated that the step 122 can be performed at different points in the manufacturing process. For example, in some embodiments, removing the separator 104 can be performed prior to inserting the substrate apparatus 120 inside a bioreactor. In other embodiments, removing the separator 104 occurs after inserting the substrate apparatus 120 inside the bioreactor. Accordingly, in some embodiments, the bioreactor may be configured to perform the various separator removal methods described above upon insertion of the substrate apparatus 120.

Figure 15A:
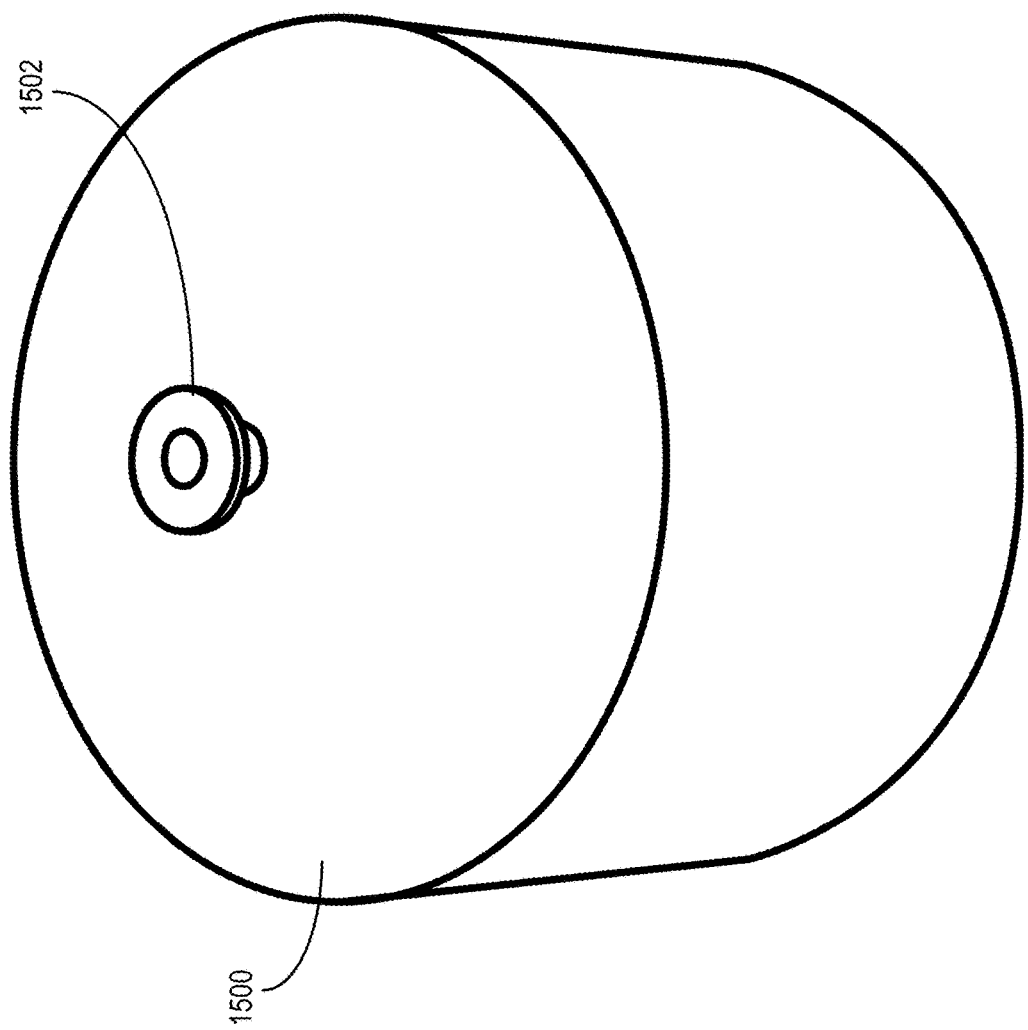
Figure 15B:
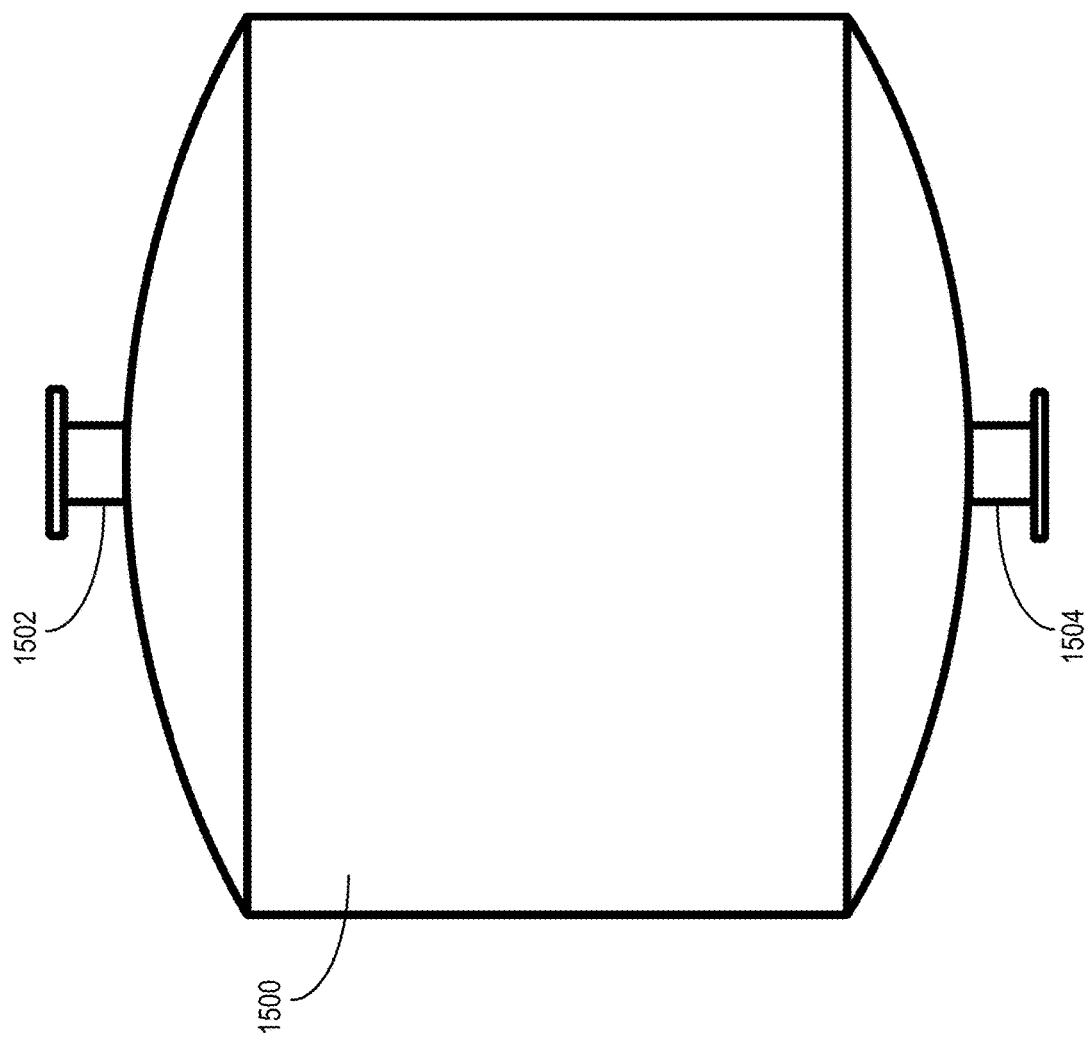

With the separator 104 removed, the locking element 118 maintains the substrate spacing between coil layers of the elongated substrate 100. Moreover, removal of the separator 104 leaves the substrate apparatus 120 prepared to receive cells and cell cultured media through coil layers exposed at the surface edge 106. Indeed, after removal of the separator 104, a seeding process can be initiated by placing the substrate apparatus 120 inside a bioreactor and flowing cells and cell cultured media therethrough. An example embodiment is described further below in relation to FIGS. 15A-15C depicting a substrate apparatus inside an example bioreactor.

Figure 2:
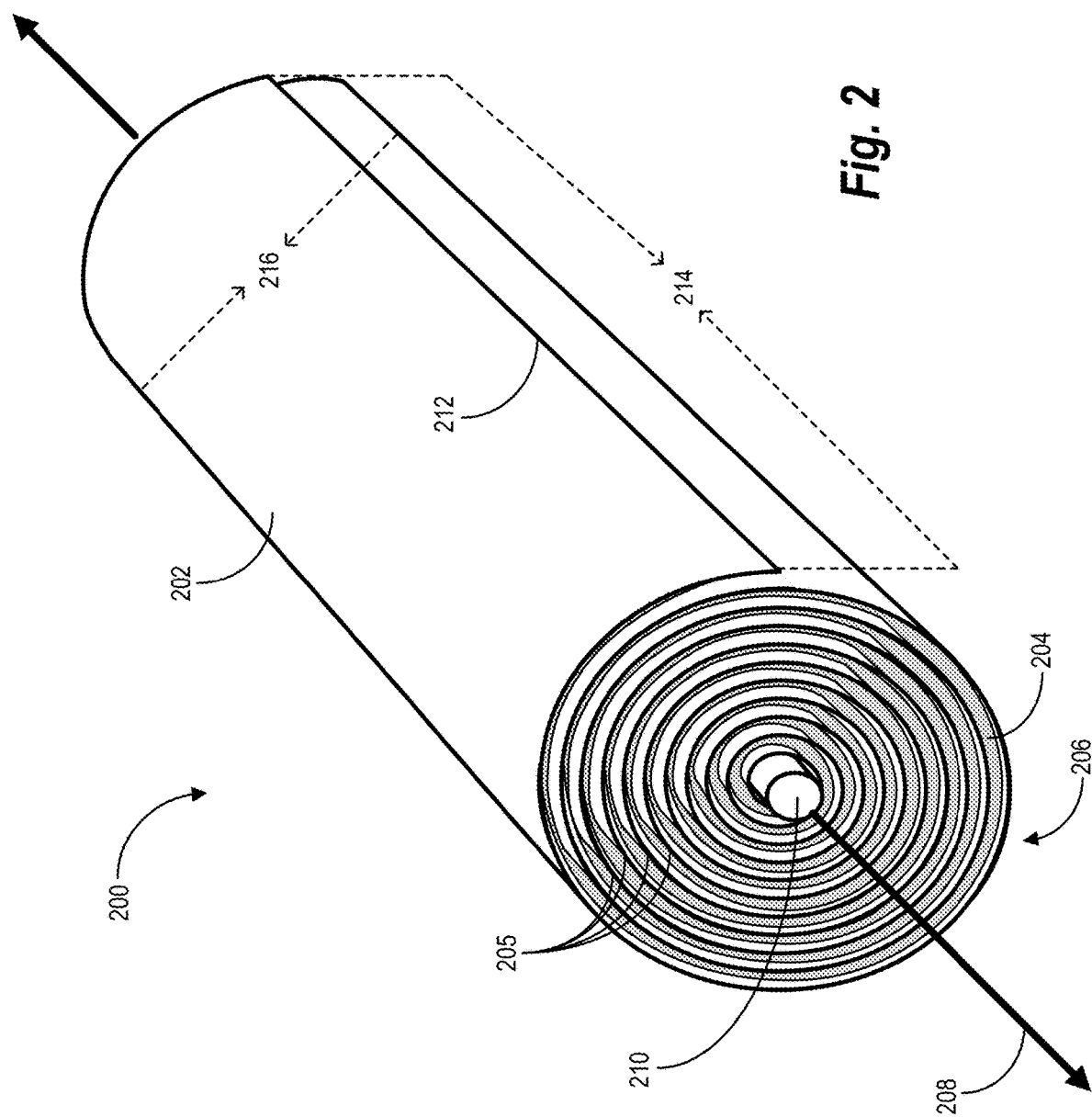
FIG. 2 illustrates a perspective side view of a substrate apparatus implementing a separator between coil layers of an elongated substrate in accordance with one or more embodiments.

FIG. 2 illustrates a perspective side view of a substrate apparatus 200 implementing a separator between coil layers of an elongated substrate in accordance with one or more embodiments. As shown in FIG. 2, the substrate apparatus 200 in the coiled configuration comprises an elongated substrate 202 with a separator 204 disposed between coil layers 205 of the elongated substrate 202. Indeed, the separator 204 provides an intra-coil spacing between the coil layers 205 that is equivalent to a thickness of the separator 204. Therefore, the intra-coil spacing between the coil layers 205 can be customized by correspondingly configuring the thickness of the separator 204. For instance, in some embodiments, the thickness of the separator 204 comprises a thickness of about 0.3 millimeters, about 1 millimeter, about 2.5 millimeters, about 10 millimeters, about 50 millimeters, about 1 centimeter, about 3 centimeters, or about 5 centimeters (or any value or range of values therebetween).

In addition to the intra-coil spacing, FIG. 2 illustrates the substrate apparatus 200 with a number of coil layers (or spirals) that corresponds to a number of turns or windings of the elongated substrate 202 about a rotational axis 208. Indeed, as shown the coil layers 205 comprises ten to eleven layers (depending on a chosen radial line between the rotational axis 208 and an outermost layer). Therefore, this configuration indicates the elongated substrate 202 was wound 10+ times.

Figure 3:
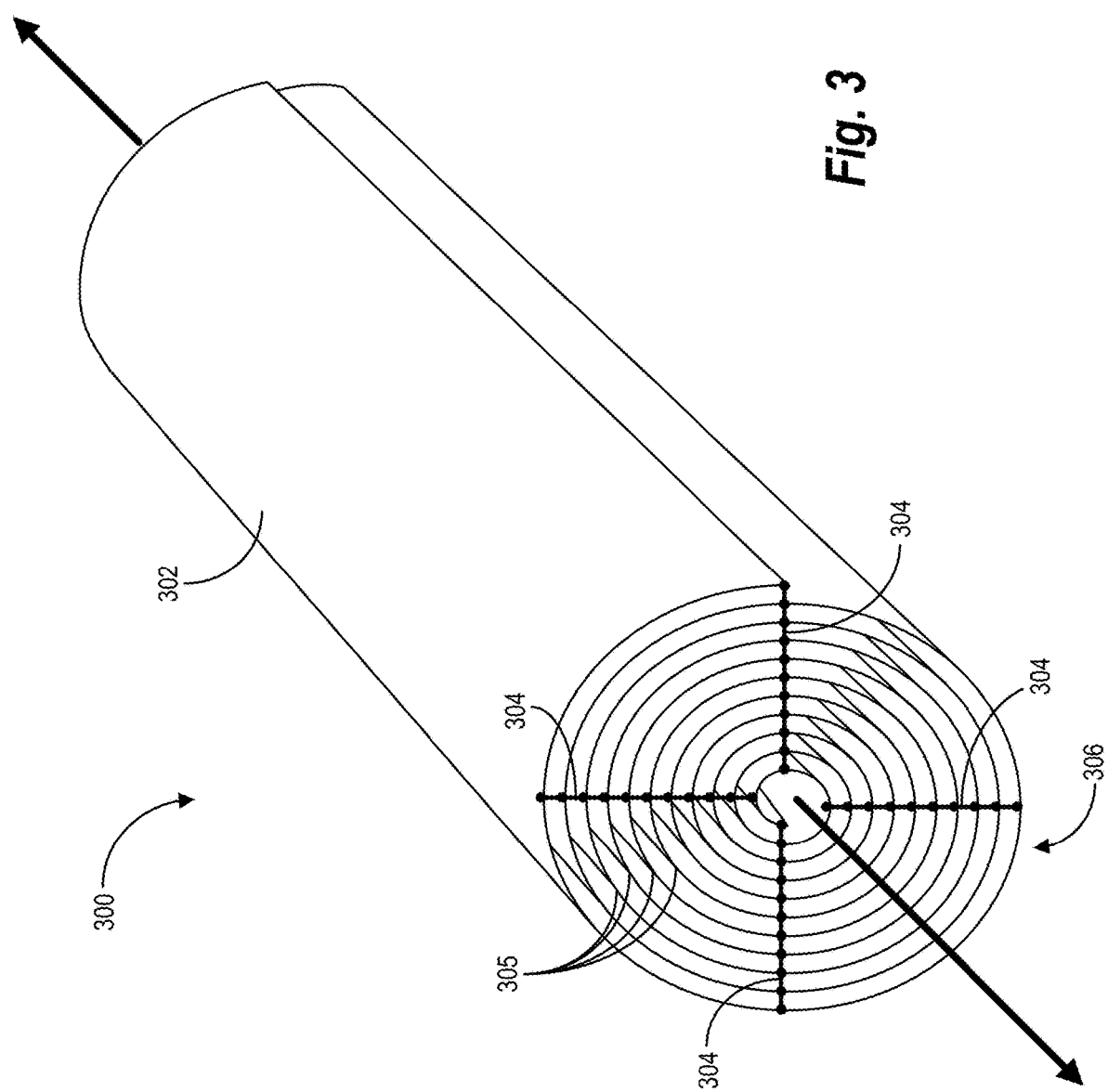
FIG. 3 illustrates a perspective side view of a substrate apparatus implementing a locking element in accordance with one or more embodiments.

However, it will be appreciated that the coil layers 205 can include different numbers of layers. For example, in some embodiments, the coil layers 205 comprise about five layers, about fifteen layers, about twenty layers, about thirty layers, about fifty layers, about one hundred layers, or more. In particular embodiments, the coil layers 205 comprise a number of layers that depends on the overall size of the substrate apparatus 200. Indeed, increasing a size of the substrate apparatus 200 may require additional locking elements to counter the increased weight (particularly at larger radial distances from the rotational axis 208). That is, each coil layer of the coil layers 205 weighs more than the previous coil layer because, as the radius gradually increases, the surface area likewise increases. Accordingly, the coil layers 205 can include a number of layers that maintains robustness, rigidity, or structural integrity of the substrate apparatus 200 (particularly after the separator 204 is removed, as shown in FIG. 3).

In some embodiments, various dimensions of the elongated substrate 202 can be adjusted (e.g., optimized for surface area and/or layer stresses). For instance, a width 214 of the substrate apparatus 200 may determine a number of layers for the coil layers 205. Specifically, as the width 214 is increased, a number of the coil layers 205 may be decreased (e.g., to prevent layer buckling or bowing mid-width between a surface edge 206 and an opposing surface not shown). In contrast, by decreasing the width 214, a diameter 216 may be increased (thereby allowing a greater number of the coil layers 205). In one example embodiment of the elongated substrate 202 in the coiled configuration, the width 214 is about thirty inches and the diameter 216 is about thirty inches. As just described though, myriad different dimensional combinations may apply.

Additionally shown in FIG. 2, the substrate apparatus 200 comprises a spool 210. Positioned along the rotational axis 208, the spool 210 is configured to help wind the elongated substrate 202 and the separator 204 together. For example, although not shown, the spool 210 may be removably affixed to at least one of the elongated substrate 202 or the separator 204 at (or near) an opposing substrate end from a substrate end 212. To illustrate, adhesives, clamps, or other attachment mechanisms bind the spool 210 to the elongated substrate 202. Thus, upon engaging the spool 210, the elongated substrate 202 and the separator 204 likewise engage and rotate about the rotational axis 208. Post-winding (as shown in FIG. 2), the spool 210 may facilitate transport or subsequent manufacturing processes with respect to the substrate apparatus 200. Additionally or alternatively, the spool 210 may be removed—leaving the core region empty as shown in FIG. 3.

Figure 6:
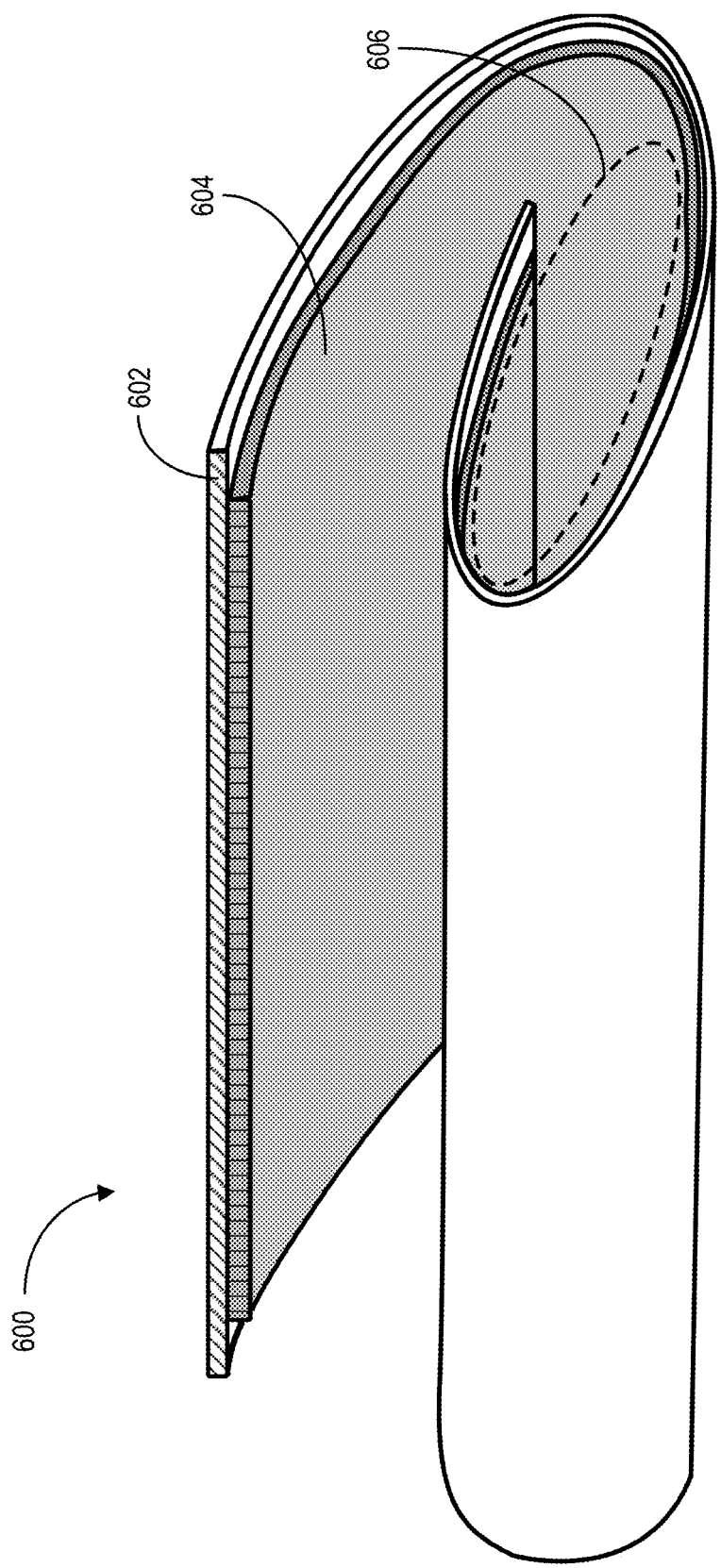
FIG. 6 illustrates a perspective view of a substrate apparatus being wound into an ovular form factor in accordance with one or more embodiments.

Further, FIG. 2 shows the spool 210 comprising a cylindrical body. Correspondingly, the substrate apparatus 200 comprises a cylindrical form factor. In other embodiments, the spool 210 comprises a different shaped body to produce different form factors of the substrate apparatus 200. For instance, in some embodiments, the spool 210 comprises a prism-shaped body for winding the substrate apparatus 200 into an ovular-form factor (e.g., as shown in FIG. 6). In other embodiments, the spool 210 comprises a triangle-shaped body, a conical-shaped body, or other polygonal-shaped body (e.g., square, pentagon, etc.).

In some embodiments, the form factor can provide certain advantages. For example, the form factor of the substrate apparatus 200 can reduce stresses of substrate layers. To illustrate, a cylindrical form factor of the substrate apparatus 200 can distribute spring forces, coil weight, etc. better than form factors with sharp corners (where material stresses can be exacerbated or unequally distributed). As another example, the form factor of the substrate apparatus 200 can influence a bioreactor efficiency (e.g., based on a volume utilization of the bioreactor). Thus, in some embodiments, the form factor of the substrate apparatus 200 matches the shape of the bioreactor for increased efficiency and volume utilization. This approach can also promote simplicity of a bioreactor design (e.g., by using a corresponding cylindrical bioreactor with a reduced number of corners or seams to seal and uniform stress distribution).

As mentioned previously, the substrate apparatus can include a separator-substrate combination wound together. After winding, a locking element can be applied to the substrate apparatus and the separator removed. In accordance with one or more such embodiments, FIG. 3 illustrates a perspective side view of a substrate apparatus 300 implementing a locking element.

As shown in FIG. 3, the substrate apparatus 300 is similar to the substrate apparatus 200 described above in relation to FIG. 2. Unlike FIG. 2, however, FIG. 3 shows an elongated substrate 302 in the coiled configuration without a separator disposed between coil layers 305. That is, FIG. 3 depicts the substrate apparatus 300 having gone through a separator removal process as described above. In addition, the substrate apparatus 300 also includes no spool (e.g., post-removal of the spool 210 described above in relation to FIG. 2).

Further shown in FIG. 3, the substrate apparatus 300 may comprise a locking element 304 attached to the coil layers 305 at a surface edge 306 of the elongated substrate 302 in the coiled configuration. In this example, the locking element 304 comprises four filaments equally spaced across the surface edge 306 and spanning from the innermost coil layer to the outermost coil layer. The four filaments comprising the locking element 304 are also spot welded perpendicularly (or substantially perpendicularly) to the surface edge 306 of the elongated substrate 302 in the coiled configuration.

In one or more embodiments, the locking element 304 maintains a position of each of the coil layers 305 relative to each other. By maintaining coil positioning, the locking element 304 allows cell cultured media to flow into the intra-coil spacing exposed at the surface edge 306 and across the substrate surface. Moreover, by affixing to the surface edge 306, the locking element 304 reduces or eliminates internal touchpoints between the coil layers 305.

Furthermore, it will be appreciated that the locking element 304 is not limited to the embodiment shown in FIG. 3. Indeed, as will be described below (e.g., in relation to FIGS. 4A-4B and FIGS. 9-11), the substrate apparatus of the present disclosure can include a variety of different types and configurations of locking elements.

As mentioned previously, the substrate apparatus can include stacked substrates (e.g., plate-like substrates that are substantially planar) as opposed to one or more spiraled or curved substrates. In accordance with one or more such embodiments, FIGS. 4A-4B illustrate side schematic views of substrate apparatuses 400a-400b that include stacked planar substrate layers. In particular, FIG. 4A shows the substrate apparatus 400a comprises substrate layers 402a-402c. The substrate layers 402a-402c are similar to the substrates described above—differing primarily in configuration. Specifically, rather than winding or coiling an individual substrate, FIG. 4A shows multiple substrates (i.e., the substrate layers 402a-402c) of a planar or flat variety stacked on top of each other.

In addition, FIG. 4A shows the substrate apparatus 400a comprises a separator 404 woven between the substrate layers 402a-402c. In particular, the separator 404 extends out from between the substrate layer 402a and the substrate layer 402b, folds back towards itself at a fold 406, and extends in between the substrate layer 402b and the substrate layer 402c. In a similar manner, the separator 404 can weave in and out from between additional substrate layers not shown. Further, in at least some cases, implementing the separator 404 as a continuous separator can improve manufacturability (e.g., by reducing a number of cutting operations to cut the separator 404). FIGS. 4A-4B are not necessarily to scale. In some embodiments, the substrate layers 402a-402c are equal in width to the separator 404, and, in other embodiments, one substrate layer may be thicker than the other substrate layer.

The substrate apparatus 400a may also include a locking element 408 attached to surface edges of the substrate layers 402a-402c. The locking element 408 is similar to the locking element 304 described above in relation to FIG. 3. Indeed, the locking element 408 maintains a position of the substrate layers 402a-402c relative to each other (e.g., to maintain a consistent spacing between substrate layers).

In the embodiment of FIG. 4A, the locking element 408 includes three struts that span between each of the substrate layers 402a-402c at different lengthwise locations along the surface edges of the substrate layers 402a-402c. However, the locking element 408 may include more or fewer struts and in different configurations and positions than presently shown.

In FIG. 4B, the substrate apparatus 400b includes the same substrate layers 402a-402c and locking element 408 as just described for the substrate apparatus 400a in FIG. 4A. Differently, however, the substrate apparatus 400b includes multiple, discrete separators 410a-410b (as opposed to a continuous separator woven between substrate layers). In particular, the separator 410a spaces apart the substrate layers 402a-402b, and the separator 410b spaces apart the substrate layers 402b-402c. In at least some embodiments, using discrete separators conserves separator material (e.g., by avoiding separator material used at the fold 406 in FIG. 4A).

The separators 410a-410b may be formed in a variety of ways. For example, in some embodiments, the separators 410a-410b are die-cut, laser-cut, or otherwise taken from a continuous sheet or roll of separator material. In other embodiments, the separators 410a-410b may be formed, molded, shaped, or constrained to certain dimensions (e.g., a length that matches a combined length and width of the substrate layers 402a-402c).

Figure 5A:
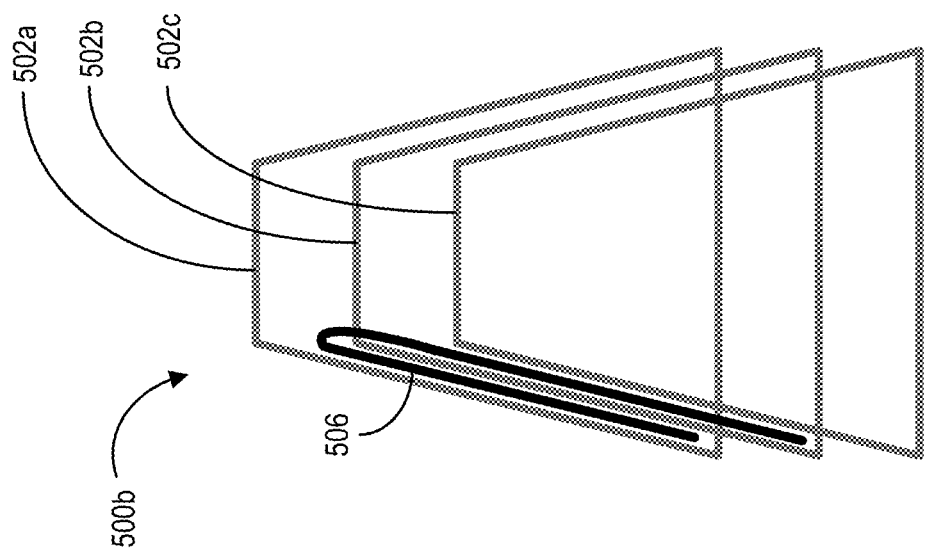
FIGS. 5A-5B illustrate cross-sectional schematic views of shaped substrates in a stacked configuration in accordance with one or more embodiments.
Figure 5B:
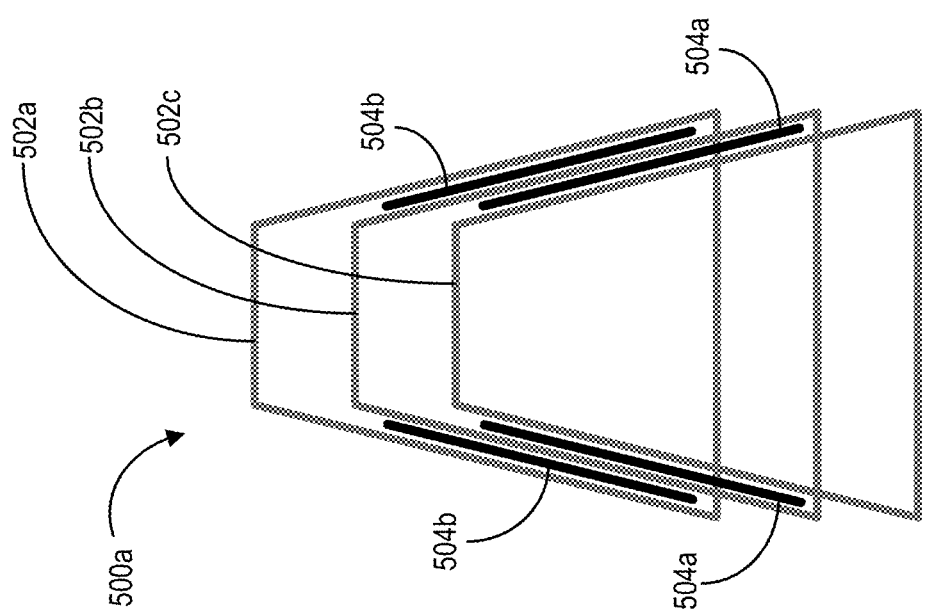

As discussed above, the substrate apparatus can include a variety of substrate configurations, including shaped substrates, stacked substrates, and/or other substrates. In accordance with one or more embodiments, FIGS. 5A-5B illustrate cross-sectional schematic views of shaped substrates in a stacked configuration. In particular, FIGS. 5A-5B show side-view cross-sections of substrate apparatuses 500a-500b that include lampshade substrates 502a-502c with a trapezoidal form factor (e.g., an isosceles trapezium form factor).

Like other substrates described above, the lampshade substrates 502a-502c include sections of bio-compatible material (e.g., stainless steel) for growing a cell mass inside a bioreactor. However, the lampshade substrates 502a-502c comprise a specific shape (e.g., that promotes cell adhesion). For example, the lampshade substrates 502a-502c provide a surface for growing cells that is angled offset from vertical, thereby increasing adherence potential against gravity.

In particular, FIG. 5A shows the substrate apparatus 500a including separators 504a-504b wrapped circumferentially around the substrate surfaces of the lampshade substrates 502a-502b. Like the separators 410a-410b discussed above, the separators 504a-504b individually space apart substrate layers. Specifically, the separator 504a spaces apart the lampshade substrates 502a-502b, and the separator 504b spaces apart the lampshade substrates 502b-502c.

In contrast, FIG. 5B shows the substrate apparatus 500b comprising the lampshade substrates 502a-502c with a separator 506 that weaves between substrates (like the separator 404 of FIG. 4A). Additionally, it will be appreciated that the separator 506 need not cover an entirety of the substrate surfaces of the lampshade substrates 502a-502b. For instance, in certain implementations, the separator 506 comprises multiple discrete separator strips interspaced around the substrate surfaces. For example, the separator 506 comprises at least two separator strips spaced apart on the substrate surfaces between the lampshade substrates 502a-502c. Due to this cross-sectional illustration, however, such discrete separator strips are not shown here. Further, in some embodiments, the separator 506 comprises a single separator strip that (although may not cover an entirety of a substrate surface) includes a separator thickness that provides a substrate spacing between the lampshade substrates 502a-502c.

Although not shown, the substrate apparatuses 500a-500b can also include locking elements that maintain a positioning of the lampshade substrates 502a-502c relative to each other. For example, one or more filaments may extend between bases of adjacently stacked lampshade substrates. Also not shown, the substrate apparatuses 500a-500b can include additional lampshade substrates (and corresponding separators) as may be desired. In another example, which is not illustrated here, the lampshade substrates have different diameters to allow smaller ones to nest inside larger ones such that stacked lampshade substrates have ends in the same plane thereby enabling planar locking elements across all ends.

As mentioned above, the substrate apparatus can include different form factors (e.g., besides a cylindrical form factor). In accordance with one or more such embodiments, FIG. 6 illustrates a perspective view of a substrate apparatus 600 being wound into an ovular form factor. In some embodiments, the ovular form factor of the substrate apparatus 600 is advantageous for certain prismatic-shaped or pouch-shaped bioreactors.

As shown in FIG. 6, the substrate apparatus 600 includes a substrate 602 and a separator 604 being wound around an oval spool 606 (indicated in dashed lines). Additionally, for ease and clarity of illustration, the substrate 602 and the separator 604 are abbreviated lengthwise (as indicated by the cross-hatching). Thus, after winding the remaining length (not shown) of the substrate 602 and the separator 604, the substrate apparatus 600 can include multiple coil layers to complete a coil configuration in the ovular form factor.

Moreover, after winding, a locking element can be added to the substrate apparatus 600 to maintain a position of the coil layers. Subsequently, the separator 604 and the oval spool 606 can be removed. In turn, the substrate apparatus 600 can be inserted into a bioreactor sized and shaped in an ovular fashion for the substrate apparatus 600.

As previously discussed, the substrate apparatus can include a variety of different separator configurations. The different separator configurations may provide more consistent substrate spacing, increase manufacturing throughput or speed, conserve separator material, and/or improve removability of the separator from between substrate layers. In accordance with one or more such embodiments, FIGS. 7A-7E illustrate plan views of substrate-separator configurations 700a-700e for winding (or alternatively, stacking). Each of the substrate-separator configurations 700a-700e in FIGS. 7A-7E includes a substrate 702 (similar to or the same as substrates discussed above). However, each of the substrate-separator configurations 700a-700e in FIGS. 7A-7E includes a different type of separator layout to be described below.

In FIG. 7A, the substrate-separator configuration 700a includes a separator 704 positioned on top of the substrate 702 and extending lengthwise in a continuous fashion between substrate ends 710. In certain embodiments, the length of the separator 704 matches or is substantially similar to the length of the substrate 702. By contrast, the separator 704 includes a smaller width than a width of the substrate 702. Indeed, the separator 704 is offset from surface edges 706-708 of the substrate 702 (e.g., with an offset of about two inches). With this offset, the separator 704 avoids interference with application of a locking element at the surface edges 706-708 of the substrate 702. For instance, without the offset, the separator 704 may inhibit formation of a proper welding bead between the locking element and the substrate 702 at the surface edges 706-708 (e.g., leading to deficient, insecure welds with cavities or unsmooth surfaces). Further, deficient welds of this type can increase contamination risks.

In FIG. 7B, the substrate-separator configuration 700b includes separator strips 712 extending widthwise at predetermined (or custom) intervals on the surface of the substrate 702. In some embodiments, the predetermined intervals (e.g., frequency or count) of the separator strips 712 can be adjusted such that a separator spacing 713 is increased or decreased. Additionally or alternatively, the separator spacing 713 may be increased or decreased by adjusting a size of the separator strips 712. For example, increasing a width of the separator strips 712 decreases the separator spacing 713, and decreasing the width of the separator strips 712 increases the separator spacing 713.

In some embodiments, it is advantageous to adjust the intervals of the separator strips 712 and/or the size of the separator strips 712 to influence the separator spacing 713. For example, decreasing the separator spacing 713 can lead to more consistent substrate spacing between coil layers. By contrast, increasing the separator spacing 713 can conserve separator material.

It will also be appreciated that the separator spacing 713 can be dynamically adjusted across the length of the 702. That is, the separator spacing 713 is not limited to constant values. To illustrate, the separator spacing 713 may progressively increase or decrease from one of the substrate ends 710 towards the other of the substrate ends 710. For instance, it may be advantageous to decrease the separator spacing 713 at a portion of the substrate 702 that will correspond to outer coil layers (e.g., to increase rigidity, prevent potential substrate touchpoints, and maintain consistent coil spacing at the outer coil layers).

Similarly, in FIG. 7C, the substrate-separator configuration 700c includes separator strips 714 extending lengthwise at predetermined (or custom) intervals on the surface of the substrate 702. The interval frequency and/or the size of the separator strips 714 affect the separator spacing 715 (e.g., as discussed above for the separator spacing 713 of FIG. 7B). In addition, by extending lengthwise (as done in FIG. 7A), the separator strips 714 of the substrate-separator configuration 700c can provide a consistent coil spacing from inner to outer coil layers. Comparatively though, the separator strips 714 of the substrate-separator configuration 700c can advantageously conserve separator material.

Figure 7E:
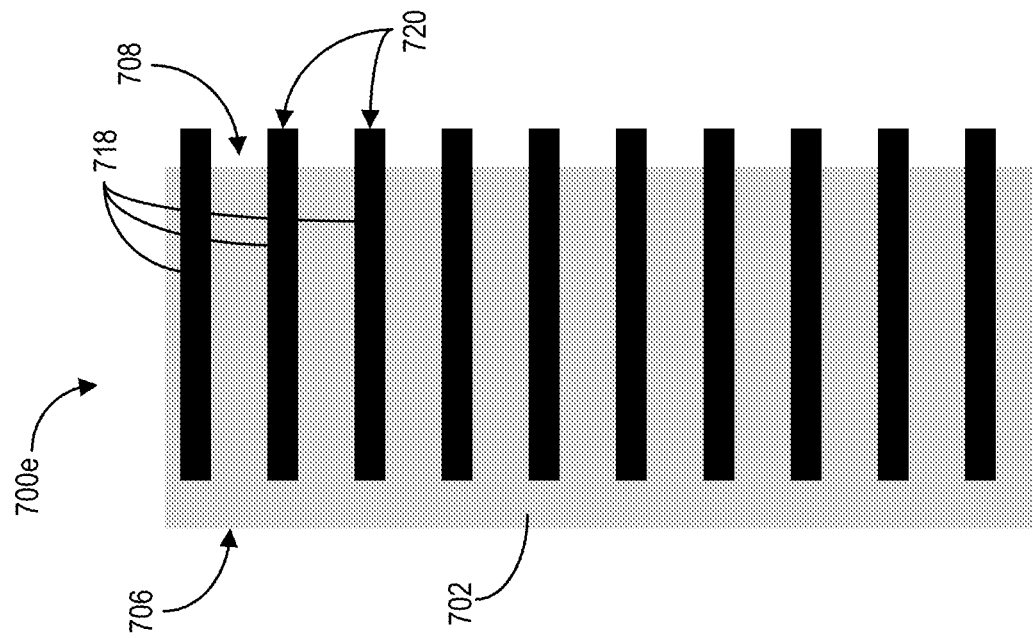
Figure 7D:
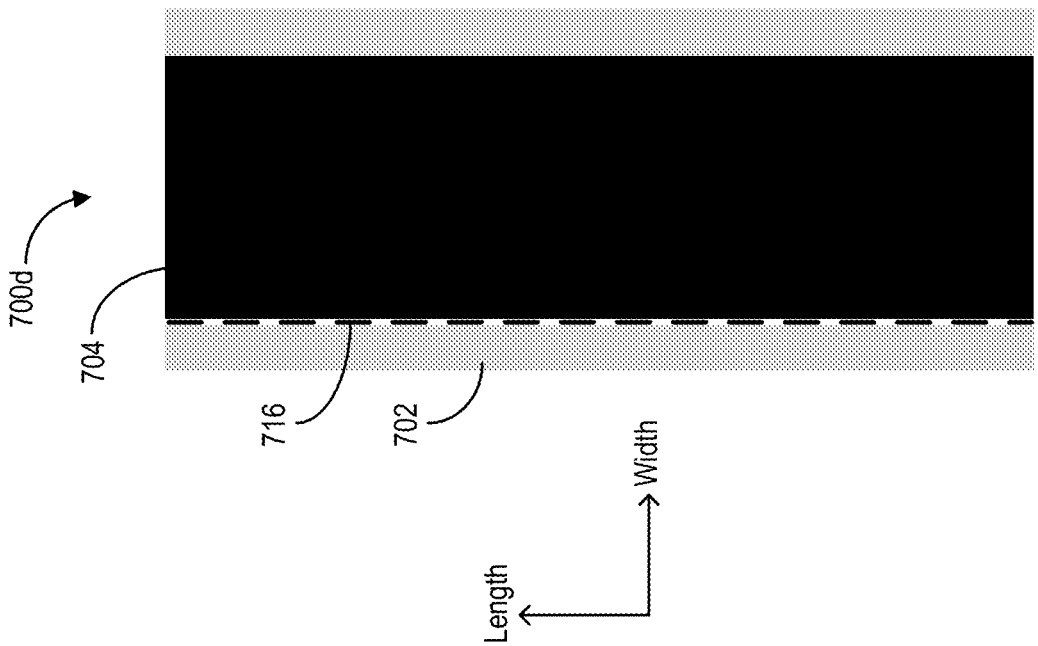

In FIG. 7D, the substrate-separator configuration 700d includes the same separator 704 positioned on top of the substrate 702 as shown in FIG. 7A. However, the substrate-separator configuration 700d includes an additional element—namely a perforated edge 716 to the separator 704. The perforated edge 716 comprises a series of lengthwise perforations along the separator 704. In particular, the perforated edge 716 facilitates a shear force (e.g., a lateral pull in the width direction) that, when applied, causes the perforations in the perforated edge 716 to easily tear. Accordingly, the perforated edge 716 can advantageously reduce an amount of shear force needed to remove the separator 704 from between coil layers.

In FIG. 7E, the substrate-separator configuration 700e includes separator strips 718 that are similar to the separator strips 712 shown in FIG. 7B. Differently, however, the separator strips 718 of the substrate-separator configuration 700e include an overhanging portion 720 that extends beyond the surface edge 708 of the substrate 702. Advantageously, the substrate-separator configuration 700e also allows for ease of separator removal. For example, after winding the substrate-separator configuration 700e, the overhanging portion 720 of the separator strips 718 may be grabbed and pulled or otherwise mechanically removed. In response to the pulling motion, the separator strips 718 may be removed from between coil layers.

As mentioned above, some embodiments of the substrate apparatus omit implementation of a separator. Instead, a locking element can be actively applied to the substrate during the winding process to create a desired intra-coil spacing (without a separator). In accordance with one or more such embodiments, FIGS. 8A-8C illustrate a process flow for forming a substrate apparatus without a separator.

Figure 8A:
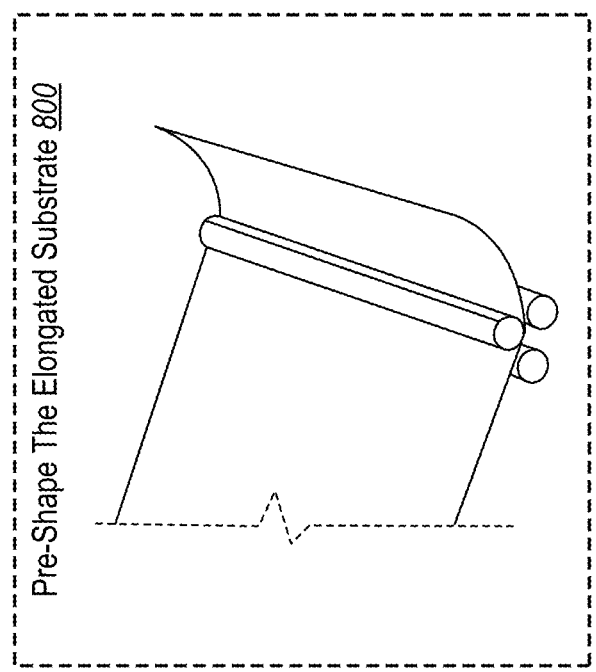
FIGS. 8A-8C illustrate a process flow for forming a substrate apparatus without a separator in accordance with one or more embodiments.
Figure 8B:
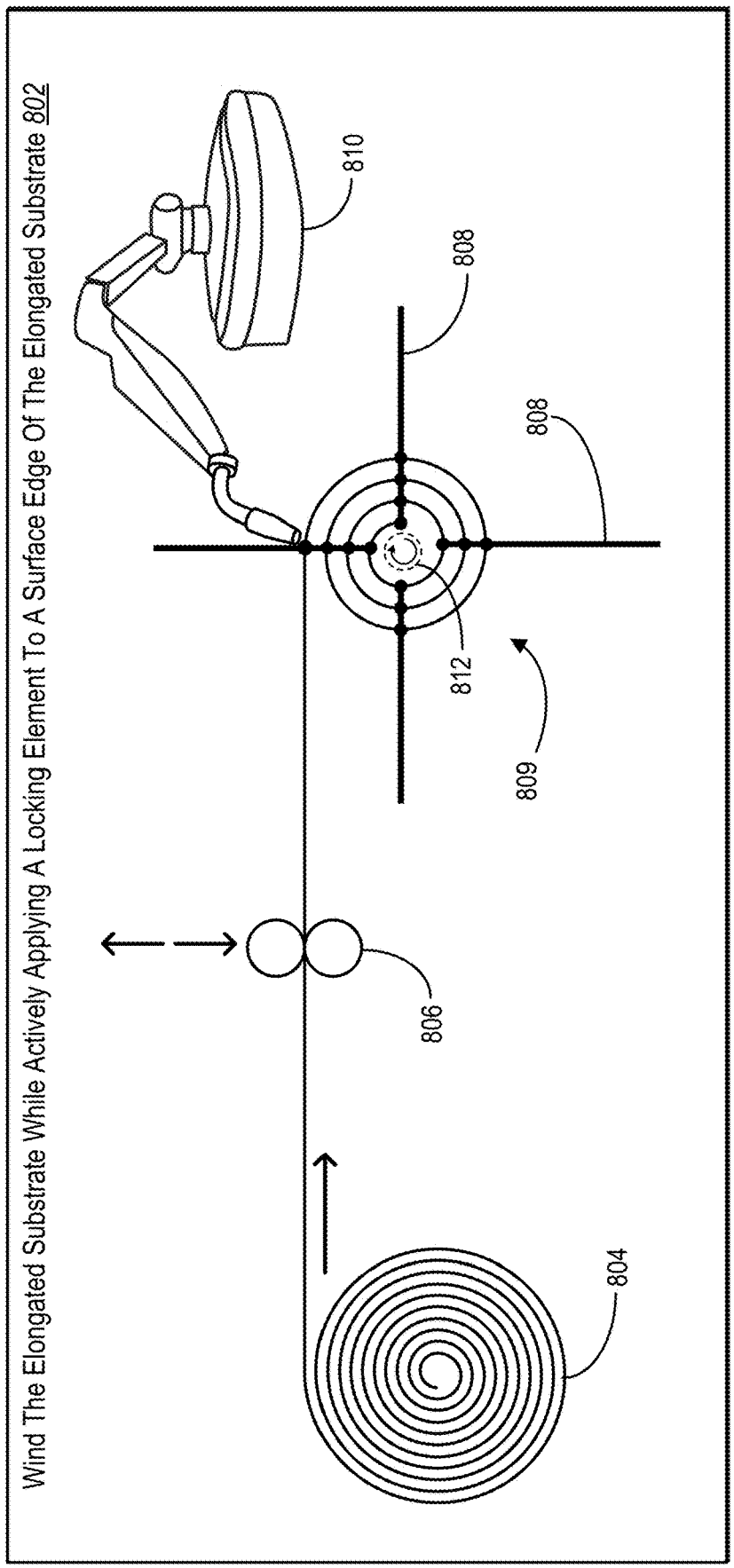
Figure 8C:
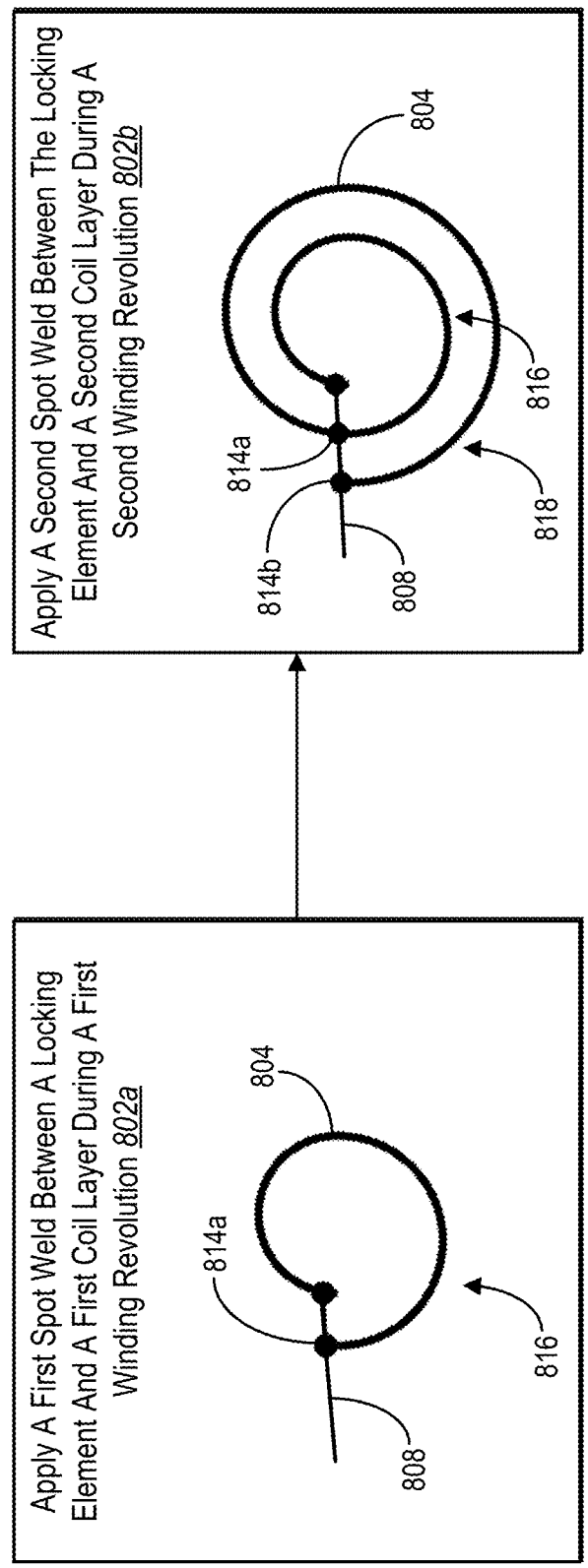

As shown in FIG. 8A, the process includes an optional step 800 of pre-shaping an elongated substrate. For example, pre-shaping the elongated substrate may include plastically deforming the elongated substrate (e.g., via a series of rollers that move relative to each other and deform the elongated substrate). Based on the plastic deformation, the elongated substrate can achieve a predetermined shape (e.g., a curved shape, one or more coils, etc.) prior to winding. Moreover, in some embodiments, the elongated substrate can be deformed into a multiple coils with an initial spacing between coil layers. In so doing, the plastic deformation and preliminary intra-coil spacing can reduce the amount of internal spring forces of the substrate apparatus when subsequently wound into tighter coils. That is, without such plastic deformation, the elongated substrate (when later wound) will have a greater tendency or spring force urging the elongated substrate to unwind. By contrast, the plastic deformation effectively resets the resting state of the elongated substrate to a coiled (or semi-coiled) configuration—thereby reducing an amount of spring force a locking element counters to maintain coil positioning.

In other embodiments, the elongated substrate is pre-shaped using other methods. For example, the elongated substrate can be overwound and/or tensioned to cause plastic deformation. Then, the elongated substrate can be released from the overwound/tensioned state such that the elongated substrate partially unwinds to a resting state. The resting state of the elongated substrate may then include multiple coils with an initial spacing between coil layers as similarly described above.

Additionally, it will be appreciated that pre-shaping the elongated substrate is not limited to a time period that precedes winding. For example, in some embodiments, the elongated substrate can be pre-shaped during the winding process. To illustrate, the elongated substrate may be pre-shaped by winding the elongated substrate according to a first tension, at least partially unwinding or detensioning the elongated substrate, and then winding or retensioning the elongated substrate according to a second tension that is less than the first tension. Similarly, in some embodiments, the elongated substrate can be pre-shaped during winding by performing an initial winding of coil layers, compressing the elongated substrate into tighter coil layers (e.g., via a press), and then completing the winding after decompression.

In FIG. 8B, at a step 802, the elongated substrate is wound while a locking element is actively applied to a surface edge of the elongated substrate. For example, at the step 802, an elongated substrate 804 passes through infeed elements 806. The infeed elements 806 include rollers that raise or lower depending on the desired positioning for affixing a locking element 808 to the elongated substrate at a surface edge 809. To illustrate, the infeed elements 806 can raise the elongated substrate 804 to increase a radial distance of a coil layer from a spool 812. In contrast, the infeed elements 806 can lower the elongated substrate 804 to decrease a radial distance of the coil layer from the spool 812. In this manner, the infeed elements 806 can dynamically control the spacing between coil layers at the surface edge 809.

Additionally shown at the step 802, a robotic system 810 can dynamically attach the locking element 808 to the surface edge 809 of the elongated substrate 804. Indeed, as the elongated substrate 804 feeds through the infeed elements 806, the spool 812 can be engaged to rotate—thereby winding the elongated substrate 804. As the elongated substrate 804 is wound around the spool 812, the robotic system 810 attaches the locking element 808 to a coil layer being wound. In some embodiments, the robotic system 810 attaches the locking element 808 simultaneously with the winding. In other embodiments, the winding pauses, and the robotic system 810 performs the next attachment between the locking element 808 and the elongated substrate 804 during the winding pause. In lieu of the robotic system 810, it will be appreciated that technicians and/or automated (or semi-automated) systems may apply the locking element 808 to the elongated substrate 804.

FIG. 8C illustrates a series of steps 802a-802b that correspond to the step 802 of FIG. 8B. In particular, the series of steps 802a-802b break down the active process of incrementally applying the locking element 808 to the elongated substrate 804 for example winding revolutions (or partial winding revolutions).

Specifically, the step 802a comprises applying a first spot weld 814a between the locking element 808 and a first coil layer 816 of the elongated substrate 804. For instance, during a first winding revolution (or at the conclusion of the first winding revolution), the robotic system 810 may generate the first spot weld 814a holding in place the first coil layer 816. For ease and clarity of illustration, the remaining portions of the elongated substrate 804 to be wound are omitted.

At the step 802b, a second spot weld 814b is applied between the locking element 808 and a second coil layer 818 of the elongated substrate 804. For example, during a second winding revolution (or at the conclusion of the second winding revolution), the robotic system 810 generates the second spot weld 814b to positionally hold the second coil layer 818 relative to the first coil layer 816.

The steps 802a-802b are repeated for subsequent coil layers. In addition, the steps 802a-802b are likewise performed for other portions (e.g., other filaments) of the locking element 808 not shown. Indeed it will be appreciated that a single coil layer can be attached to multiple filaments of the locking element 808 at different points along the coil layer. In this manner, a desired configuration of the locking element can be formed. Moreover, by dynamically applying the locking element 808 with each winding revolution, the substrate apparatus can be incrementally formed without a separator.

Figure 9:
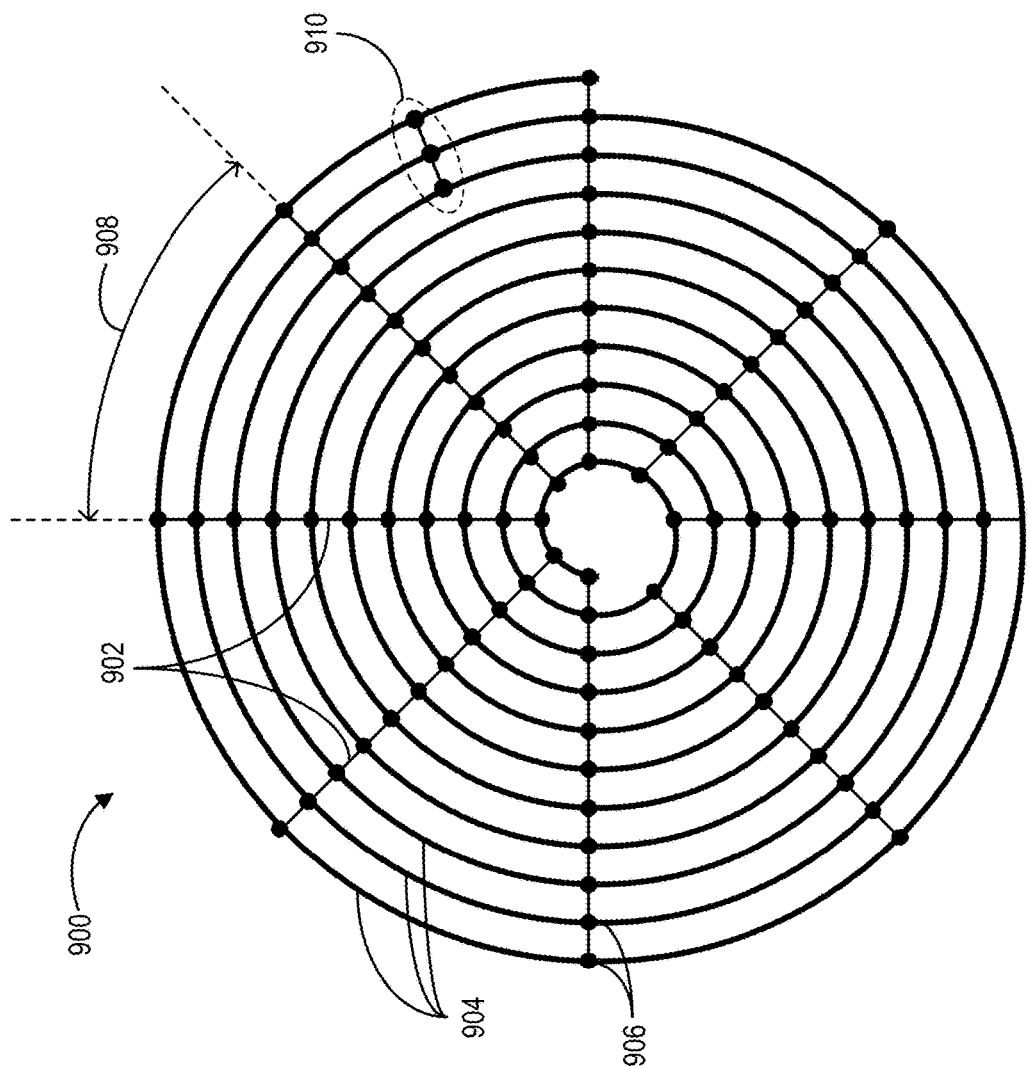
FIGS. 9-11 illustrate side views of substrate apparatuses with different locking elements in accordance with one or more embodiments.
Figure 10:
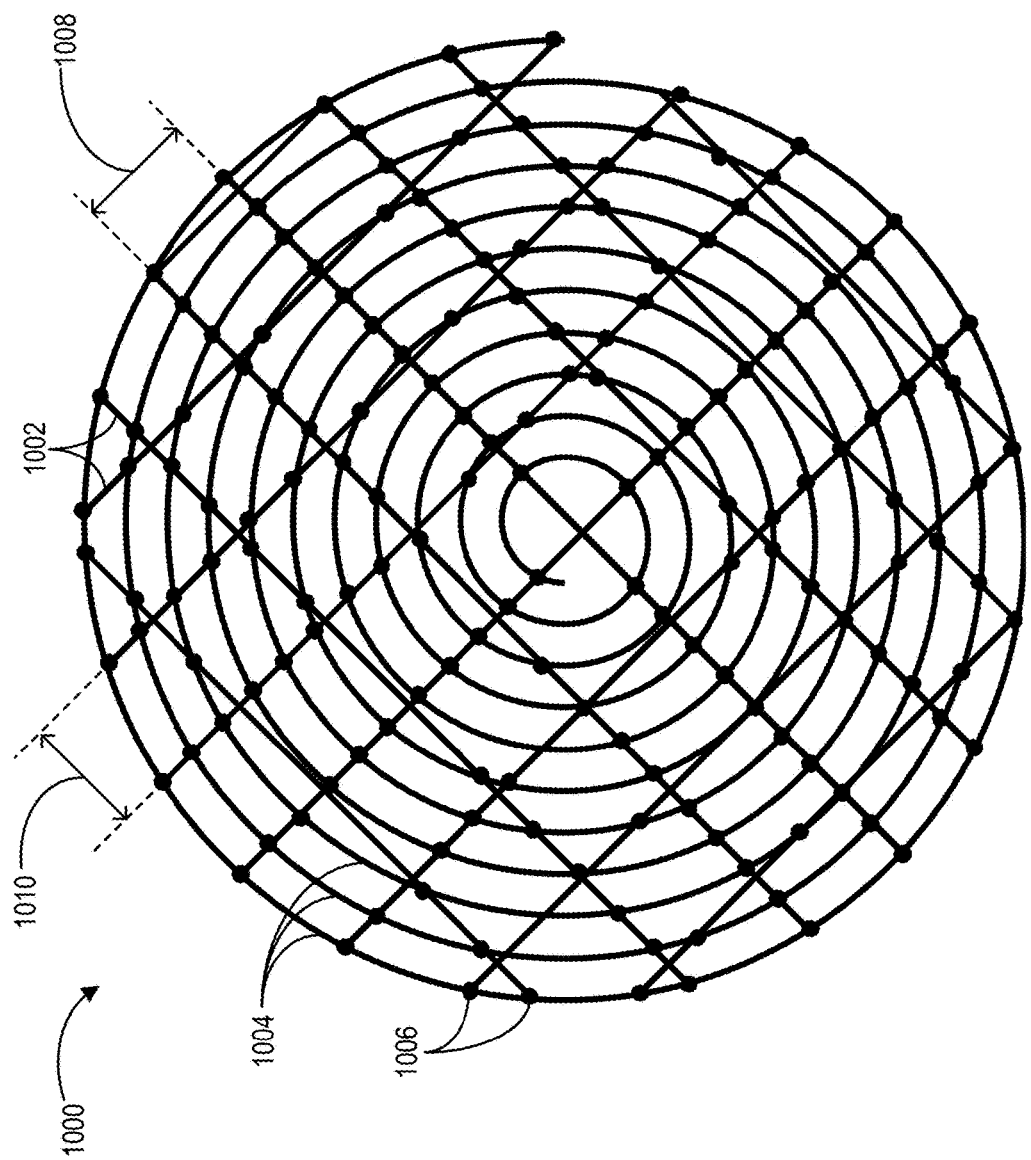
Figure 11:
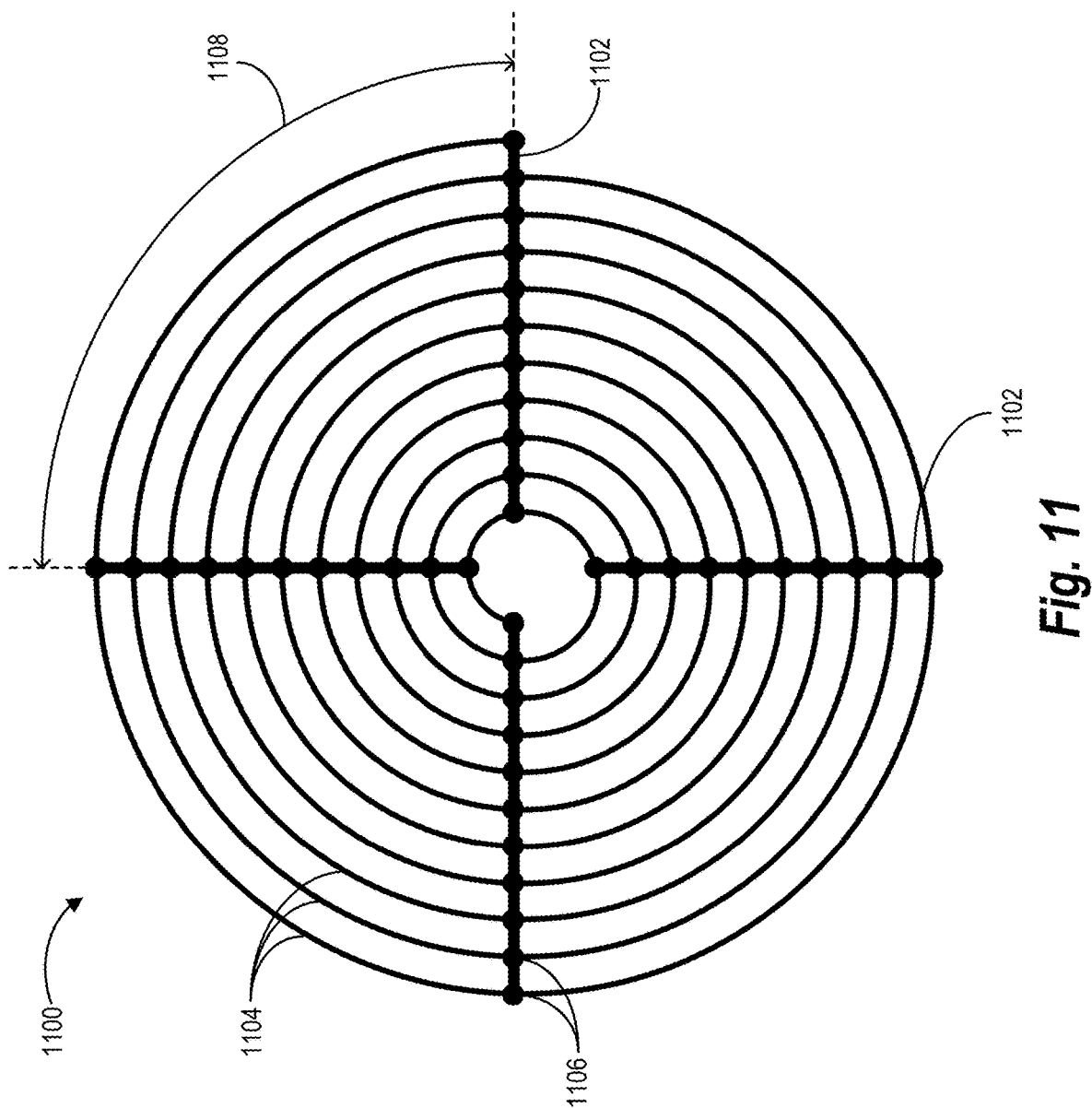

As discussed above, the substrate apparatus can include a variety of different locking element configurations. FIGS. 9-11 illustrate side views of substrate apparatuses 900-1100 with different locking elements in accordance with one or more embodiments.

In FIG. 9, the substrate apparatus 900 includes a locking element 902 configured in a spider-web formation. In particular, the locking element 902 attaches to coil layers 904 at attachment sites 906. In some embodiments, the attachment sites 906 comprise spot welds. In other embodiments, the attachment sites 906 comprise a brazed joint, a soldered joint, or other suitable type of joint (e.g., interlocking joints, mating joints, magnetic joints, glued joints, and the like). For instance, in certain implementations, the locking element 902 may be attached to the coil layers 904 at the attachment sites 906 via a biocompatible molten metal (e.g., that has a lower melting point than the coil layers 904).

In addition, the locking element 902 itself can include a variety of different structures. As shown, the locking element 902 includes a set of rigid or flexible (wire-like) metal filaments that traverse across the coil layers 904 in a perpendicular manner. However, in other embodiments, the locking element 902 comprises rigid struts or support arms. Similarly, the locking element 902 can include different gauges, diameters, operating loads (tension), maximum loads, etc. in order to maintain the positioning of the coil layers 904 relative to each other.

Moreover, each filament, strut, or component of the locking element 902 comprises an angular spacing interval 908. The angular spacing interval 908 can be modified as may be desired (e.g., to increase coil rigidity). In at least some embodiments, the angular spacing interval 908 is about forty-five degrees.

Additionally shown in FIG. 9, the coil layers 904 have increasingly larger arc lengths as the coil layers spiral outwardly from the innermost coil layer. That is, coil layer distance between two attachment sites increases as a coil layer's radial distance from the spiral center increases. Thus, in some embodiments, intermediate locking elements 910 may be added to outer coil layers with larger coil layer distances between attachment sites. For example, the intermediate locking elements 910 may be added where a coil layer distance between two attachment sites satisfies a threshold distance. As another example, the intermediate locking elements 910 may be added where an intra-coil spacing deviates by a threshold amount (e.g., to maintain an intra-coil spacing). In this manner, the intermediate locking elements 910 can be added to provide increased coil rigidity and help prevent substrate touchpoints.

FIG. 10 illustrates the substrate apparatus 1000 optionally comprising a locking element 1002 configured in a grid-type formation. In particular, the locking element 1002 attaches to coil layers 1004 at attachment sites 1006 in a same or similar manner as just described above in relation to FIG. 9. Further, the locking element 1002 can include the same or similar components (e.g., filaments, struts, etc.) as the locking element 902 of FIG. 9.

As shown in FIG. 10 though, the locking element 1002 optionally comprises more filaments and corresponding attachment sites to form a grid pattern. Indeed, the filaments of the locking element 1002 include a grid spacing 1008-1010 that can be modified (e.g., increased or decreased) to achieve a desired rigidity and/or intra-coil spacing between the coil layers 1004. Similarly, the grid spacing 1008-1010 can be varied across the coil layers 1004 (e.g., smaller grid intervals at outer coil layers and larger grid intervals at inner coil layers).

With increased coverage across the coil layers 1004, the locking element 1002 can provide increased structural rigidity to the substrate apparatus 1000. For instance, the locking element 1002 can better distribute spring forces from the coil layers 1004. In turn, the locking element 1002 can more easily maintain the coil positioning of the coil layers 1004. However, like a grate or screen, in some embodiments, the locking element 1002 affects fluid flow (e.g., cultured cell media, harvested tissue, etc.). Therefore, in certain implementations, increased fluid flow or more robust cleaning methods may be utilized with the locking element 1002.

FIG. 11 illustrates the substrate apparatus 1100 comprising a locking element 1102 configured in a "t" formation or "X" formation. In particular, the locking element 1102 attaches to coil layers 1104 at attachment sites 1106 in a same or similar manner as described above in relation to FIG. 9. In addition, the locking element 1102 can include the same or similar components (e.g., filaments, struts, etc.) as the locking element 902 of FIG. 9.

Unique to FIG. 11 however, the locking element 1102 comprises four discrete filaments (or struts) with an angular spacing interval 1108. The angular spacing interval 1108 can be modified (e.g., by adding or removing filaments). In at least some embodiments, the angular spacing interval 1108 is about ninety degrees. Additionally, in some embodiments, intermediate locking elements may be added (e.g., to increase rigidity at outer coil layers as shown in FIG. 9).

As mentioned above, the substrate apparatus can include a variety of additional or alternative embodiments that are contemplated within the scope of the present disclosure. In accordance with one or more such embodiments, FIG. 12 illustrates a side view of a substrate apparatus 1200 with inner, intermediate, and outer support structures.

As shown in FIG. 12, the substrate apparatus 1200 optionally comprises a locking element 1202 connected to a first set of coil layers 1210 and a second set of coil layers 1212 corresponding to one or more substrates. The locking element 1202 connects to the first set of coil layers 1210 and the second set of coil layers 1212 at various attachment sites in a same or similar fashion as previously discussed.

In addition, the substrate apparatus 1200 may comprise an inner support structure 1204, an intermediate support structure 1206, and an outer support structure 1208. The inner support structure 1204, the intermediate support structure 1206, and the outer support structure 1208 can include a variety of different materials or components that increase rigidity of the substrate apparatus 1200. In certain implementations, the inner support structure 1204, the intermediate support structure 1206, and the outer support structure 1208 include a same or similar material as the locking element 1202 or the sets of coil layers 1210-1212. For example, in some embodiments, the inner support structure 1204 comprises a solid metal rod (or alternatively, a hollowed core with a reinforced sidewall). In addition, the intermediate support structure 1206 and the outer support structure 1208 can include rigid cylindrical shells, such as a metal material (e.g., stainless steel) of thicker gauge compared to the first set of coil layers 1210 and the second set of coil layers 1212.

To provide the increased rigidity, the substrate apparatus 1200 may connect the inner support structure 1204, the intermediate support structure 1206, and the outer support structure 1208 to other components. Indeed, as shown in FIG. 12, the locking element 1202 connects to each of the inner support structure 1204, the intermediate support structure 1206, and the outer support structure 1208 (e.g., via spot welds, brazing, and the like).

In addition, the first set of coil layers 1210 and the second set of coil layers 1212 also connect to the support structures as similarly described above via spot welds, brazing, and the like. The first set of coil layers 1210 is disposed between the inner support structure 1204 and the intermediate support structure 1206. Accordingly, the first set of coil layers 1210 connects to the intermediate support structure 1206 at attachment site 1214a (e.g., a first spot weld). In additional or alternative embodiments, the first set of coil layers 1210 also connects to the inner support structure 1204. Further, the second set of coil layers 1212 is disposed between the intermediate support structure 1206 and the outer support structure 1208. Accordingly, the second set of coil layers 1212 connects to the intermediate support structure 1206 at attachment site 1214b (e.g., a second spot weld) and to the outer support structure 1208 at attachment site 1214c (e.g., a third spot weld). In this manner, the inner support structure 1204, the intermediate support structure 1206, and the outer support structure 1208 can provide increased rigidity to both the locking element 1202 and the first and second sets of coil layers 1210-1212.

As previously mentioned, one or more embodiments of the substrate apparatus include permanent types of separators positioned on the substrate surface. Although these embodiments introduce touchpoints between substrate layers or coils, certain configurations of permanent separators can still reduce a number of touchpoints for separating substrate layers or coils. Moreover, certain configurations of permanent separators can be implemented to mitigate touchpoints at the majority of tissue growth areas on the substrate surface. In accordance with one or more such embodiments, FIGS. 13A-13B respectively illustrate plan and side views of a substrate-separator configuration 1300 with permanent separator nubs.

Figure 13A:
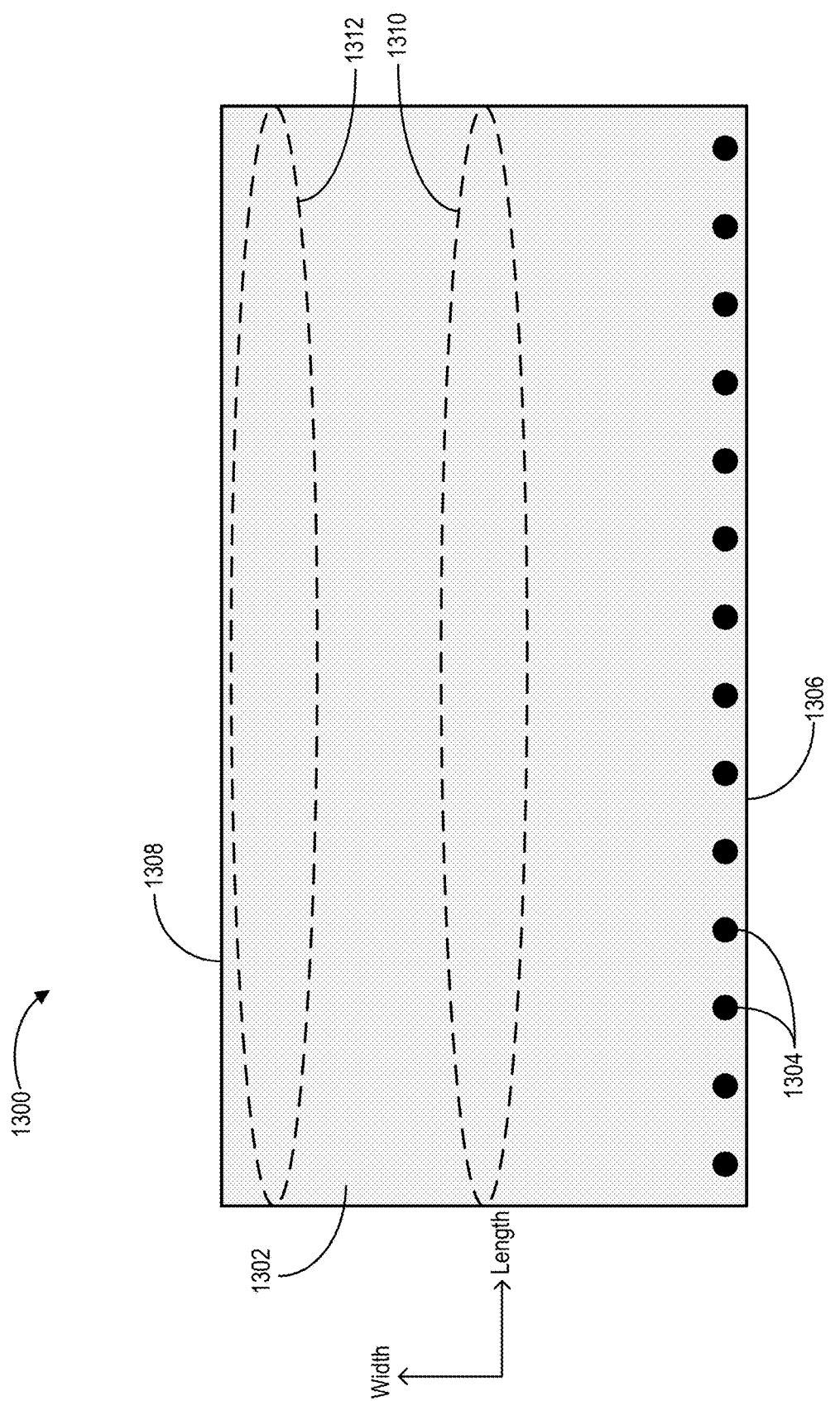
FIGS. 13A-13B respectively illustrate plan and side views of a substrate-separator configuration with permanent separator nubs in accordance with one or more embodiments.

In FIG. 13A, the substrate-separator configuration 1300 comprises a substrate 1302 with permanent separator nubs 1304 positioned lengthwise along the surface of the substrate 1302 near a surface edge 1306. Additionally or alternatively, in some embodiments, the permanent separator nubs 1304 may be positioned at a center region 1310 and/or an edge region 1312 near a surface edge 1308 opposite from the surface edge 1306. In certain implementations, placing additional permanent separator nubs in the center region 1310 and/or the edge region 1312 can provide increased rigidity and/or more consistent intra-coil spacing when later wound into a coiled configuration. In some cases, the permanent separator nubs can reduce the surface area on the substrate surface for growing cells. However, the substrate-separator configuration 1300 can advantageously reduce surface touch points between substrate layers or coils by positioning the permanent separator nubs 1304 primarily along the surface edge 1306 (and/or the surface edge 1308).

Additionally, it will be appreciated that the permanent separator nubs 1304 can include a variety of different materials. For example, in some embodiments, the permanent separator nubs 1304 comprise a biocompatible metal material (e.g., stainless steel). Similarly, the permanent separator nubs 1304 can be permanently affixed to the surface of the substrate 1302 in various ways—including welding, brazing, bonding, and the like.

Figure 13B:
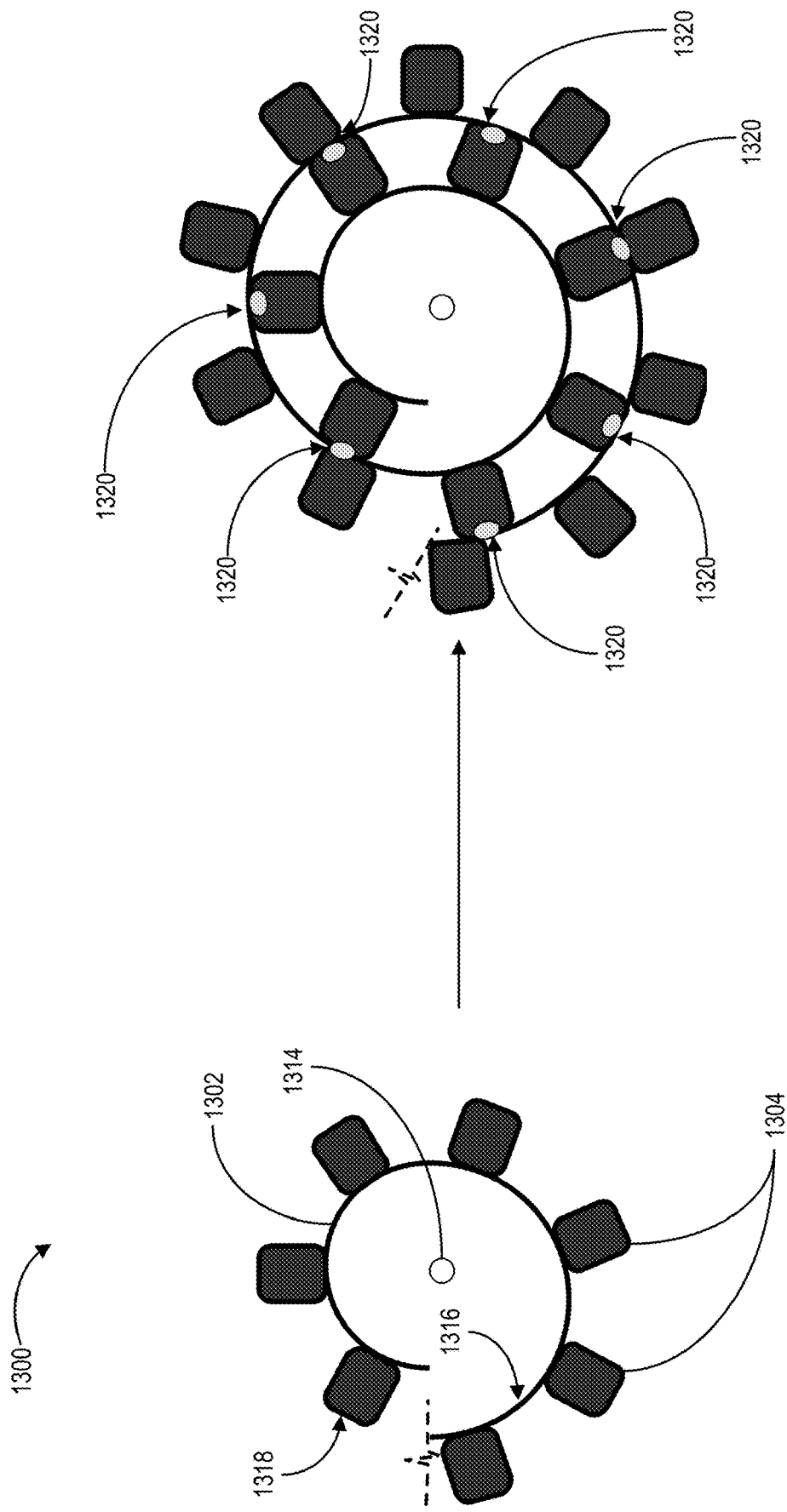

FIG. 13B depicts the substrate-separator configuration 1300 being wound into a coiled configuration by winding the substrate 1302 about a rotational axis 1314. More particularly, as the substrate 1302 is being wound, the permanent separator nubs 1304 are positioned such that a top surface 1318 of each permanent separator nub interfaces with an underside surface 1316 of the substrate 1302. These interface points can become attachment sites 1320, for example, by welding together the top surface 1318 of each permanent separator nub and the underside surface 1316 of the substrate 1302. Alternatively, the attachment sites 1320 can include a brazed joint, a bonded joint, and the like. Furthermore, the attachment sites 1320 can be actively fabricated during the winding process or upon completion of the winding process (as may be desired).

Figure 14:
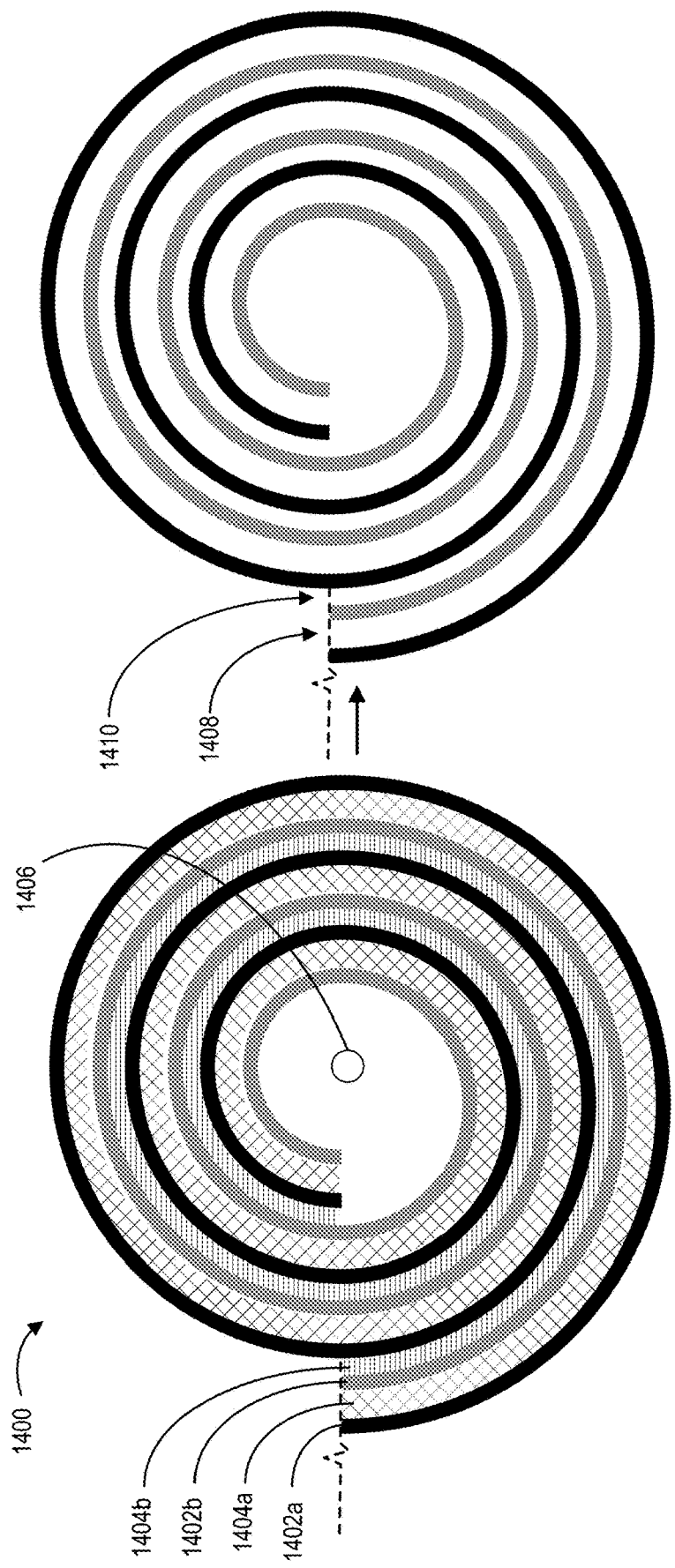
FIG. 14 illustrates a side view of substrate apparatus with parallel substrates in a coiled configuration in accordance with one or more embodiments.

As mentioned above, one or more embodiments of the substrate apparatus include parallel substrates spiraled together (e.g., to provide multi-channel fluid flow). In accordance with one or more such embodiments, FIG. 14 illustrates a side view of a substrate apparatus 1400 with parallel substrates 1402a-1402b in a coiled configuration. Although only two substrates are shown here for simplicity's sake, it is contemplated that more than two substrates may be wound in a parallel configuration.

As shown, the parallel substrates 1402a-1402b are initially spaced apart via a separators 1404a-1404b. Both the parallel substrates 1402a-1402b and the separators 1404a-1404b may be the same as or similar to the substrates and separators discussed above. Further shown, both the parallel substrates 1402a-1402b and the separators 1404a-1404b are spiraled together about a rotational axis 1406.

Subsequently, in a separator removal process, the separators 1404a-1404b are removed to provide fluid channels 1408-1410 defined by the substrates 1402a-1402b. The fluid channels 1408-1410 are separate fluid channels of different lengths. Indeed, in the coiled configuration of the substrate apparatus 1400 (which is truncated for illustration purposes), the fluid channel 1408 completes three turns (or revolutions) starting from the center and spiraling outward. In comparison, the fluid channel 1410 completes two turns starting from the center and spiraling outward. Therefore, the fluid channel 1410 has a shorter channel length compared to a channel length for the fluid channel 1408—due to the fluid channel 1408 having comparatively tighter (i.e., smaller) turn radii.

Advantageously, the differing lengths of the fluid channels 1408-1410 provides different fluid flow properties that can be leveraged for different fluid flow. For example, in some embodiments, the fluid channels 1408-1410 can be utilized for different speeds of fluid flow. As another example, the fluid channels 1408-1410 can be utilized for different directions of fluid flow. It will therefore be appreciated that the fluid channels 1408-1410 can be utilized in myriad ways and for various applications.

As discussed previously, the substrate apparatus can be inserted inside a bioreactor for growing a cell mass. In accordance with one or more such embodiments, FIGS. 15A-15C illustrate a bioreactor 1500 for implementing with a substrate apparatus. In particular, FIGS. 15A-15B respectively illustrate a perspective view and a side view of the bioreactor 1500. As shown, the bioreactor 1500 comprises an inlet 1502 and an outlet 1504 configured for fluid transmission. In some embodiments, the inlet 1502 and the outlet 1504 are directional such that fluid proceeds into the bioreactor 1500 via the inlet 1502 and out of the bioreactor 1500 via the outlet 1504. In other embodiments, the inlet 1502 and the outlet 1504 are not directional such that fluid flow is reversable. Additional or alternative implementations of a bioreactor are disclosed in U.S. Patent Pub. No. 2021/0145031 A1, entitled APPARATUSES AND METHODS FOR PREPARING A MEAT PRODUCT, filed on Nov. 20, 2020, (hereafter, the "'031 Publication"), the contents of which are expressly incorporated herein by reference.

FIG. 15C illustrates a cut-away view of the bioreactor 1500. In particular, FIG. 15C shows the bioreactor 1500 comprises an internal cavity or enclosure sized and shaped for housing a substrate apparatus 1506 (interchangeable with any substrate apparatus disclosed herein). In some embodiments, the internal cavity or enclosure of the bioreactor 1500 comprises a volume between about 25 liters and about 20,000 liters. In particular embodiments, the bioreactor 1500 comprises an internal volume of about 500 liters.

Additionally, it will be appreciated that the bioreactor 1500 can be oriented in a variety of ways. For example, in some embodiments, the bioreactor 1500 is oriented at a vertical offset (e.g., as disclosed in the '031 Publication). In other embodiments, the bioreactor 1500 is oriented horizontally or at a horizontal offset. Still, in other embodiments, the bioreactor 1500 is oriented based on a certain process being performed (e.g., seeding, harvesting, cleaning, etc.). Additionally or alternatively, the bioreactor 1500 is oriented based on the coil configuration and/or corresponding form factor. Similarly, in some embodiments, the bioreactor 1500 is oriented based on the number of coil layers. For instance, if the substrate apparatus 1506 has a threshold number of coil layers, the bioreactor 1500 may be positioned at a threshold angle relative to the vertical or horizontal so as to help maintain the intra-coil spacing and avoid causing layer bowing or buckling.

Figure 16:
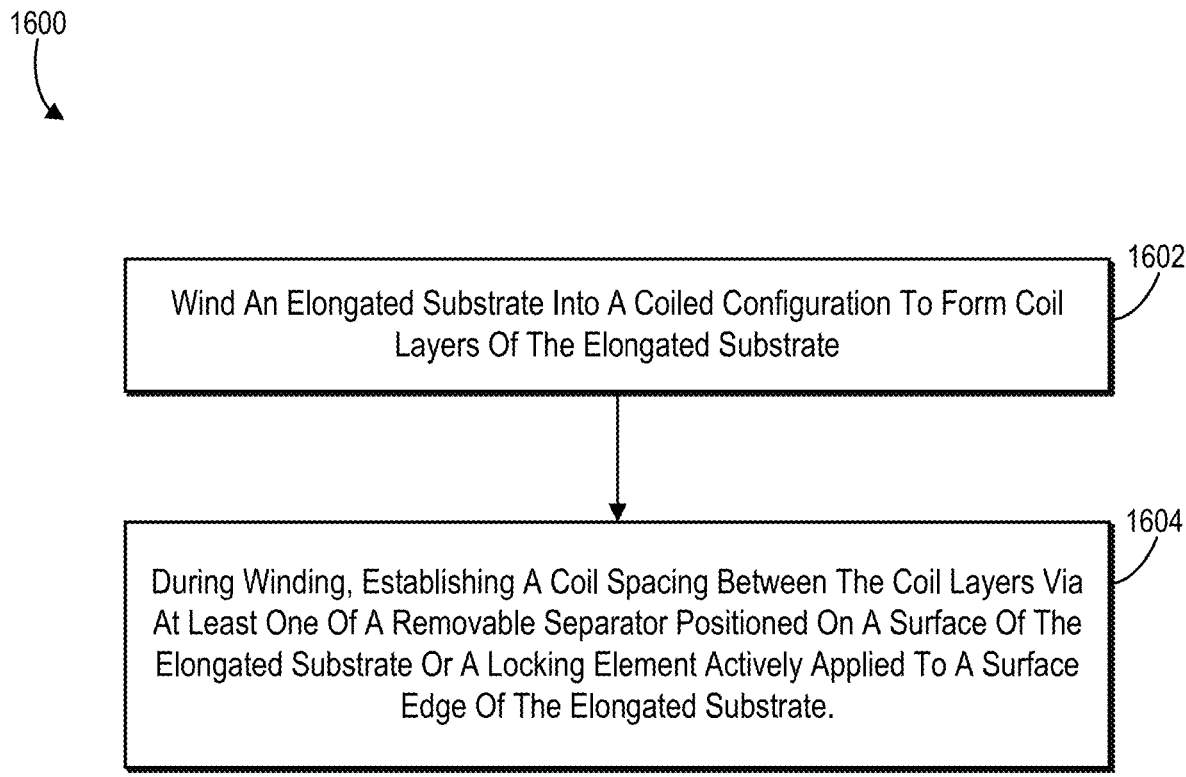
FIG. 16 illustrates a flowchart of a series of acts for manufacturing a substrate apparatus in accordance with one or more embodiments.

FIGS. 1-15, the corresponding text, and the examples provide several different systems, methods, techniques, components, and/or devices relating to the substrate apparatus in accordance with one or more embodiments. In addition to the above description, one or more embodiments can also be described in terms of flowcharts including acts for manufacturing a particular apparatus. For example, FIG. 16 illustrates a flowchart of a series of acts 1600 for manufacturing a substrate apparatus to insert into a bioreactor to grow a cell mass in accordance with one or more embodiments. The substrate apparatus may be manufactured according to one or more acts of the series of acts 1600 in addition to or alternatively to one or more acts described in conjunction with other figures. While FIG. 16 illustrates acts according to one embodiment, alternative embodiments may omit, add to, reorder, and/or modify any of the acts shown in FIG. 16.

As shown, the series of acts 1600 includes an act 1602 of winding an elongated substrate into a coiled configuration to form coil layers of the elongated substrate.

The series of acts 1600 also includes an act 1604 of during winding, establishing a coil spacing between the coil layers via at least one of a removable separator positioned on a surface of the elongated substrate or a locking element actively applied to a surface edge of the elongated substrate.

It is understood that the outlined acts in the series of acts 1600 are only provided as examples, and some of the acts may be optional, combined into fewer acts, or expanded into additional acts without detracting from the essence of the disclosed embodiments. Additionally, the acts described herein may be repeated or performed in parallel with one another or in parallel with different instances of the same or similar acts. As an example, an additional or alternative act in the series of acts 1600 may include an act of, prior to winding, applying the removable separator to the surface of the elongated substrate by: applying a continuous sheet of a spacing material to substantially cover the surface of the elongated substrate; or applying a plurality of strips of the spacing material positioned at predetermined intervals along a length or a width of the surface of the elongated substrate, wherein a thickness of the removable separator controls the coil spacing.

As another example, an additional or alternative act in the series of acts 1600 may include an act of, during winding, positioning the coil layers to include the coil spacing between the coil layers by adjusting one or more infeed elements to control the coiled configuration for each coil layer; and actively attaching the locking element to the coil layers at predetermined increments of a winding revolution.

As a further example, an additional or alternative act in the series of acts 1600 may include an act of adjusting the one or more infeed elements to control the coiled configuration for each coil layer by raising or lowering one or more infeed rollers to control a diameter of each coil layer.

In still another example, an additional or alternative act in the series of acts 1600 may include an act of actively attaching the locking element to the coil layers by: applying a first spot weld between a filament and a first coil layer during a first winding revolution; and applying a second spot weld between the filament and a second coil layer during a second winding revolution.

Additionally, another example of an additional or alternative act in the series of acts 1600 may include an act of: winding the elongated substrate into the coiled configuration by winding the elongated substrate around a rotational axis, the coil layers of the elongated substrate being exposed at the surface edge along the rotational axis; and locking the elongated substrate in the coiled configuration by applying the locking element to a plurality of coil layers at the surface edge.

In another example of an additional or alternative act, the series of acts 1600 may include an act of: winding the elongated substrate into the coiled configuration by simultaneously winding the removable separator positioned on the surface of the elongated substrate around the rotational axis; and after applying the locking element, at least partially removing the removable separator from between the coil layers via at least one of heat treatment, chemical treatment, or physical displacement.

In particular embodiments, an additional or alternative act in the series of acts 1600 includes an act of removing the removable separator via chemical treatment by partially dissolving the removable separator such that a film remains on the surface of the elongated substrate, wherein the film provides an adhesive surface for cells.

As another example, an additional or alternative act in the series of acts 1600 may include an act of applying the locking element by attaching one or more filaments to the plurality of coil layers in an attachment configuration that permits fluid flux for seeding or harvesting a cell mass through the locking element at the surface edge.

In yet another example, an additional or alternative act in the series of acts 1600 may include an act of, prior to winding or during winding, plastically deforming the elongated substrate.

In a further example, an additional or alternative act in the series of acts 1600 may include an act of forming an apparatus for inserting into a bioreactor to grow a cell mass, the apparatus comprising: an elongated substrate wound in a coiled configuration to form coil layers of the elongated substrate; a removable separator positioned on a surface of the elongated substrate to space apart the coil layers; and a locking element affixed to a surface edge of the elongated substrate, the locking element configured to maintain a position of the coil layers.

Additionally, in another example of an additional or alternative act, the series of acts 1600 may include an act of forming an apparatus comprising: the elongated substrate wound around a rotational axis, the coil layers of the elongated substrate being exposed at the surface edge along the rotational axis; and the locking element affixed to a plurality of coil layers at the surface edge of the elongated substrate.

In yet another example, an additional or alternative act in the series of acts 1600 may include an act of forming an apparatus comprising a locking element with one or more filaments attached via spot welding or brazing to the coil layers exposed at the surface edge, the one or more filaments being perpendicular to the surface edge and traversing across the coil layers.

In a further example, an additional or alternative act in the series of acts 1600 may include an act of forming an apparatus comprising a removable separator that includes: a continuous sheet that substantially covers the surface of the elongated substrate; or a plurality of strips positioned at predetermined intervals along a length or a width of the surface of the elongated substrate.

In still another example, an additional or alternative act in the series of acts 1600 may include an act of forming an apparatus that comprises a removable separator configured for at least partial removal from between the coil layers via at least one of heat treatment, chemical treatment, or physical displacement.

In particular embodiments, an additional or alternative act in the series of acts 1600 includes an act of forming an apparatus that comprises a removable spool around which the elongated substrate is wound in the coiled configuration, wherein: the removable spool comprises a spool shape that includes a polygonal shape, a cylindrical shape, a conical shape, or a prismatic shape; and a shape of the elongated substrate wound in the coiled configuration corresponds to the spool shape.

In another example, an additional or alternative act in the series of acts 1600 may include an act of forming an apparatus for inserting into a bioreactor to grow a cell mass, the apparatus comprising: a first substrate layer and a second substrate layer in a stacked configuration such that the second substrate layer is positioned on top of the first substrate layer; a removable separator positioned between the first substrate layer and the second substrate layer to space apart the first substrate layer and the second substrate layer; and a locking element affixed to surface edges of the first substrate layer and the second substrate layer, the locking element configured to maintain a position of the first substrate layer and the second substrate layer relative to each other.

In yet another example, an additional or alternative act in the series of acts 1600 may include an act of forming an apparatus comprising a third substrate layer in the stacked configuration such that the third substrate layer is positioned on top of the second substrate layer and the first substrate layer, wherein the removable separator continuously weaves between each of the first substrate layer, the second substrate layer, and the third substrate layer by extending out from between the first substrate layer and the second substrate layer and folding back over on top of the second substrate layer to space apart the second substrate layer and the third substrate layer.

In a further example, an additional or alternative act in the series of acts 1600 may include an act of forming an apparatus such that: the removable separator is configured for removal from between the first substrate layer and the second substrate layer via at least one of heat treatment, chemical treatment, or physical displacement; and the locking element is configured to maintain a position of the first substrate layer relative to the second substrate layer independent of the removable separator.

Additionally, in another example of an additional or alternative act, the series of acts 1600 may include an act of forming an apparatus such that: the first substrate layer and the second substrate layer comprise sheets of metal; and the locking element comprises one or more metal filaments spot welded or brazed to the surface edges of the first substrate layer and the second substrate layer.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The present invention may be embodied in other specific forms without departing from its spirit or essential characteristics. Indeed, the described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A method of manufacturing an apparatus for growing a cell mass in a bioreactor, the method comprising:
   winding an elongated substrate into a coiled configuration to form coil layers of the elongated substrate; and
   during winding, establishing a coil spacing between the coil layers via a locking element actively applied to a surface edge of the elongated substrate, the coil spacing comprising a gap between adjacent layers of the coil layers.

2. The method of claim 1, further comprising:
   prior to winding, applying a removable separator to a surface of the elongated substrate by:
   applying a plurality of strips of a spacing material positioned at predetermined intervals along a length or a width of the surface of the elongated substrate,
   wherein a thickness of the removable separator controls the coil spacing.

3. The method of claim 1, wherein during winding, positioning the coil layers to include the coil spacing between the coil layers comprises:
   adjusting one or more infeed elements to control the coiled configuration for each coil layer; and
   actively attaching the locking element to the coil layers at predetermined increments of a winding revolution.

4. The method of claim 3, wherein adjusting the one or more infeed elements to control the coiled configuration for each coil layer comprises raising or lowering one or more infeed rollers to control a diameter of each coil layer.

5. The method of claim 3, wherein actively attaching the locking element to the coil layers comprises:
   applying a first spot weld between a filament and a first coil layer during a first winding revolution; and
   applying a second spot weld between the filament and a second coil layer during a second winding revolution.

6. The method of claim 1, wherein:
   winding the elongated substrate into the coiled configuration comprises winding the elongated substrate around a rotational axis, the coil layers of the elongated substrate being exposed at the surface edge along the rotational axis;
   wherein the method further comprises locking the elongated substrate in the coiled configuration by applying the locking element to a plurality of coil layers at the surface edge.

7. The method of claim 6, wherein:
   winding the elongated substrate into the coiled configuration comprises simultaneously winding a removable separator positioned on a surface of the elongated substrate around the rotational axis;
   wherein the method further comprises, after applying the locking element, at least partially removing the removable separator from between the coil layers via at least one of heat treatment, chemical treatment, or physical displacement.

8. The method of claim 7, wherein removing the removable separator via chemical treatment comprises partially dissolving the removable separator such that a film remains on the surface of the elongated substrate, wherein the film provides an adhesive surface for cells.

9. The method of claim 6, wherein applying the locking element comprises attaching one or more filaments to the plurality of coil layers in an attachment configuration that permits fluid flux for seeding or harvesting a cell mass through the locking element at the surface edge.

10. The method of claim 1, further comprising: prior to winding or during winding, plastically deforming the elongated substrate.

* * * * *